(12) United States Patent
Vilhelmsen

(10) Patent No.: US 10,335,369 B2
(45) Date of Patent: Jul. 2, 2019

(54) COMPOSITIONS COMPRISING A DELIVERY AGENT AND PREPARATION THEREOF

(71) Applicant: Novo Nordisk A/S, Bagsvaerd (DK)

(72) Inventor: Thomas Vilhelmsen, Karslunde (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/386,218

(22) PCT Filed: Mar. 15, 2013

(86) PCT No.: PCT/EP2013/055363
§ 371 (c)(1),
(2) Date: Sep. 18, 2014

(87) PCT Pub. No.: WO2013/139695
PCT Pub. Date: Sep. 26, 2013

(65) Prior Publication Data
US 2015/0031606 A1    Jan. 29, 2015

Related U.S. Application Data

(60) Provisional application No. 61/748,844, filed on Jan. 4, 2013.

(30) Foreign Application Priority Data

Mar. 22, 2012 (EP) .................................... 12160742
Jan. 31, 2013 (EP) .................................... 13153422

(51) Int. Cl.
| | | |
|---|---|---|
| A23C 1/05 | (2006.01) | |
| A61K 9/16 | (2006.01) | |
| A61K 38/26 | (2006.01) | |
| A61K 9/20 | (2006.01) | |

(52) U.S. Cl.
CPC .......... *A61K 9/1617* (2013.01); *A61K 9/1682* (2013.01); *A61K 9/2013* (2013.01); *A61K 9/2077* (2013.01); *A61K 9/2095* (2013.01); *A61K 38/26* (2013.01)

(58) Field of Classification Search
None
See application file for complete search history.

(56) References Cited

U.S. PATENT DOCUMENTS

| | | | |
|---|---|---|---|
| 5,773,647 A | 6/1998 | Leone-Bay et al. | |
| 5,866,536 A | 2/1999 | Leone-Bay et al. | |
| 7,049,283 B2 | 5/2006 | Ault et al. | |
| 8,039,018 B2 | 10/2011 | Majuru et al. | |
| 8,053,429 B2 | 11/2011 | Cumming et al. | |
| 9,278,123 B2 | 3/2016 | Sauerberg et al. | |
| 9,993,430 B2 | 6/2018 | Jensen et al. | |
| 2005/0009748 A1 | 1/2005 | Dinh et al. | |
| 2005/0148497 A1 | 7/2005 | Khan | |
| 2006/0078622 A1* | 4/2006 | Majuru ................ | A61K 9/145 424/489 |
| 2006/0286129 A1 | 12/2006 | Sarubbi | |
| 2007/0049557 A1 | 3/2007 | Ahmed et al. | |
| 2007/0224262 A1* | 9/2007 | Majuru ................ | A61K 9/1617 424/456 |
| 2008/0153779 A1 | 6/2008 | Liao et al. | |
| 2008/0194676 A1 | 8/2008 | Abbas et al. | |
| 2008/0255250 A1 | 10/2008 | Gomez-Orellana et al. | |
| 2009/0124639 A1 | 5/2009 | Oyewumi et al. | |
| 2009/0156478 A1 | 6/2009 | Lau et al. | |
| 2010/0016229 A1 | 1/2010 | Sarubbi | |
| 2010/0151009 A1 | 6/2010 | Levchik | |
| 2010/0210526 A1 | 8/2010 | Joshi | |
| 2011/0142800 A1 | 6/2011 | Kidron et al. | |
| 2011/0218148 A1 | 9/2011 | Azria et al. | |
| 2013/0345134 A1 | 12/2013 | Sauerberg et al. | |
| 2015/0072926 A1 | 3/2015 | Vilhelmsen et al. | |
| 2015/0150811 A1 | 6/2015 | Jensen et al. | |
| 2016/0067184 A1 | 3/2016 | Nielsen et al. | |
| 2016/0151462 A1 | 6/2016 | Sauerberg et al. | |
| 2018/0360918 A1 | 12/2018 | Sauerberg et al. | |

FOREIGN PATENT DOCUMENTS

| | | |
|---|---|---|
| CN | 101010339 A | 8/2007 |
| JP | 2004131398 A | 4/2004 |
| JP | 2007-536268 A | 12/2007 |
| JP | 2008-509933 A | 4/2008 |
| JP | 2009542711 A | 12/2009 |
| JP | 2011509077 A | 3/2011 |
| JP | 2012-121923 A | 6/2012 |
| JP | 2013543814 A | 12/2013 |
| JP | 2014503526 A | 2/2014 |

(Continued)

OTHER PUBLICATIONS

He Xiaorong et al., Mechanistic Study of the Effect of Roller Compaction and Lubricant on Tablet Mechanical Strength, Journal: Journal of Pharmaceutical Sciences, Year: 2007, vol. 96, No. 5, pp. 1342-1355.

Mollan Jr. Matthew J. et al., The effects of lubrication on the compaction and post-compaction properties of directly compressible maltodextrins, Journal: International Journal of Pharmaceutics, Year: 1996, vol. 144, Issue 1, pp. 1-9.

Rowe Raymond C et al., Book: Handbook of Pharmaceutical Excipients, Title: Acesulfame Potassium, Edition—5th, Year: 2006, Complete book.

(Continued)

*Primary Examiner* — Satyanarayana R Gudibande
(74) *Attorney, Agent, or Firm* — Nonna G. Akopyan

(57) ABSTRACT

The invention relates to granules and pharmaceutical compositions comprising a salt of N-(8-(2-hydroxybenzoyl) amino)caprylic acid and a lubricant obtained by mixing hereof for more than 5 minutes prior to granulation as well as processes for their preparation and use thereof in medicine.

6 Claims, No Drawings

Specification includes a Sequence Listing.

(56) References Cited

FOREIGN PATENT DOCUMENTS

| | | | |
|---|---|---|---|
| JP | 2015-515459 A | 5/2015 | |
| RU | 2158138 C2 | 10/2000 | |
| RU | 2226402 C2 | 4/2004 | |
| WO | 200048589 A1 | 8/2000 | |
| WO | 200050012 A1 | 8/2000 | |
| WO | 200141737 A2 | 6/2001 | |
| WO | 2003005944 A1 | 1/2003 | |
| WO | 03/072195 A2 | 9/2003 | |
| WO | 2005004900 A1 | 1/2005 | |
| WO | 2005107773 A2 | 11/2005 | |
| WO | 2006/097537 A2 | 9/2006 | |
| WO | 2006103661 A2 | 10/2006 | |
| WO | 2006124047 A2 | 11/2006 | |
| WO | 2007093226 A1 | 8/2007 | |
| WO | 2007117706 A2 | 10/2007 | |
| WO | 2007146234 A2 | 12/2007 | |
| WO | 2008020096 A1 | 2/2008 | |
| WO | 2008039351 A2 | 4/2008 | |
| WO | 2008109385 A2 | 9/2008 | |
| WO | 2009032749 A2 | 3/2009 | |
| WO | 2009/050738 A2 | 4/2009 | |
| WO | 2010/020978 A1 | 2/2010 | |
| WO | 2010/092163 A2 | 8/2010 | |
| WO | 2011084618 A2 | 7/2011 | |
| WO | 2011094531 A1 | 8/2011 | |
| WO | 2011109787 A1 | 9/2011 | |
| WO | 2011116139 A2 | 9/2011 | |
| WO | 2011138421 A1 | 11/2011 | |
| WO | 2012080471 A1 | 6/2012 | |

OTHER PUBLICATIONS

Steinert R E et al., Orally Administered Glucagon-Like Peptide-1 Affects Glucose Homeostasis Following an Oral Glucose Tolerance Test in Healthy Male Subjects, Journal: Clinical Pharmacology and Therapeutics, Year: 2009, vol. 86, No. 6, pp. 644-650.

von Eggelkraut-Gottanka Stephan G. et al., Roller Compaction and Tabletting of St. John's Wort Plant Dry Extract Using a Gap Width and Force Controlled Roller; Compactor. II. Study of Roller Compaction Variables on Granule and Tablet Properties by a 33 Factorial Design, Journal: Pharmaceutical Development and Technology, Year: 2002, vol. 7, No. 4, pp. 447-455.

Beglinger C et al., Clinical Pharmacology and Therapeutics,"Pharmacokinetics and Pharmacodynamic Effects of Oral GLP-1 and PYY3-36: A Proof-of-Concept Study in Healthy Subjects"., 2008, vol. 84, No. 4, pp. 468-474.

Steinert RE et al, American Journal of Clinical Nutrition,"Oral Administration of Glucagon-Like Peptide 1 or Peptide YY 3-36 Affects Food Intake in Healthy Male Subjects", 2010, vol. 92, pp. 810-817.

Maher Sam et al., Overcoming poor permeability: translating permeation enhancers for oral peptide delivery, Journal: Drug Discovery Today:Technologies, Year: 2011, vol. 9, No. 2, pp. e113-e119.

Maher Sam et al., Safety and efficacy of sodium caprate in promoting oral drug absorption: from in vitro to the clinic, Journal: Advanced Drug Delivery Reviews, Year: 2009, vol. 61, pp. 1427-1449.

Michel Marre et al., GLP-1 receptor agonists today, Journal: Diabetes Research; and Clinical Practice, Year: 2011, vol. 93, No. 3, pp. 317-327.

Walsch Edwin G et al., Oral delivery of macromolecules: rationale underpinning Gastrointestinal Permeation Enhancement Technology (GIPET®), Journal: Therapeutic Delivery, Year: 2011, vol. 2, No. 12, pp. 1595-1610. OTH.

Makoto Otsuka, Chemoinformetrical evaluation of granule and tablet properties of pharmaceutical preparations by near-infrared spectroscopy, "Chemometrics and Intelligent Laboratory Systems" Year 2006, vol. 82, No. 1-2, pp. 109-114.

Shah R. B et al. Process Analytical Technology: Chemometric Analysis of Raman and Near Infra-red Spectroscopic Data for Predicting Physical Properties of Extended Release Matrix Tablets, "Journal of Pharmaceutical Sciences" Year 2007, vol. 96, No. 5, pp. 1356-1365.

Aenugu H.P.R et al. Near Infra Red Spectroscopy—An Overview, "International Journal of ChemTech Research" Year 2011, vol. 3, No. 2, pp. 825-836.

Donoso M et al. Prediction of Tablet Hardness and Porosity Using Near-Infrared Diffuse Reflectance Spectroscopy as a Nondestructive Method, "Pharmaceutical Development and Technology" Year 2003, vol. 8, No. 4, pp. 357-366.

Jeckel et al. Importance of particle size knowledge for tablet porosity determination by NIRS, "Tablet Tech Seminar, FMC Biopolymer" Year 2007, retrieved from the Internet: URL:http://www.pharmtech.uni-bonn.de/forschung/arbeitskreis-porf-steffens/download-16, the whole document.

Remington, The Science and Practice of Pharmacy, 22nd Edition, 2012.

Felix Kratz "A Clinical Update of Using Albumin as a Drug Vehicle—A Commentary" Journal of Controlled Release 2014 vol. 190 pp. 331-336.

Leonard Thomas W et al., Promoting absorption of drugs in humans using medium-chain fatty acid-based solid dosage forms:GIPET™, Journal: Expert Opinion Drug Delivery, Year: 2006, vol. 3(5), pp. 685-692.

Rivera et al. Oral Delivery of Heparin in Combination with Sodium N-[8-(2-Hydroxybenzoyl)amino]caprylate: Pharmacological Considerations. Pharmaceutical Research 1997 vol. 14 No. 12 pp. 1830-1834.

Su Young Chae et al. "Preparation, Characterization and Application of Biotinylated and Biotin-PEGylated Glucagon-Like Peptide-1 Analogues for Enhanced Oral Delivery." Bioconjugate Chemistry 2008 vol. 19 No. 1 pp. 334-341.

Emisphere Technologies. "Carriers Enhance Drug Delivery" Manufacturing Chemistry 1999 vol. 70 No. 6 pp. 25-26.

Adam W. G. Alani et al., "Mechanistic Understanding of Oral Drug Absorption Enhancement of Cromolyn Sodium by an Amino Acid Derivative," Pharmaceutical Research, 2008, vol. 25, No. 1, pp. 48-54.

Bhansali et al., "Historical Overview of Incretin Based Therapies," Supplement to JAPI, 2010, vol. 58, pp. 10-14.

Valentino et al., "Central and Peripheral Molecular Targets for Antiobesity Pharmacotherapy," Clinical Pharmacology and Therapeutics, 2010, vol. 87, No. 6, pp. 652-662.

Bastin et al., "Salt Selection and Optimisation Procedures for Pharmaceutical New Chemical Entities," Org Proc Res & Devt, 2000, vol. 4, pp. 427-435.

Drug Data Report, 2006, vol. 28, p. 933.

Keck et al., Moderne Pharmazeutische Technologie, 2009, pp. 8-14.

Kidron et al., "A Novel Per-Oral Insulin Formulation: Proof of Concept Study in Non-Diabetic Subjects," Diabetic Medicine, 2004, vol. 21, pp. 354-357.

Letter to Sandoz International GmbH regarding English translation of claim of patent JP4585037, dated Aug. 29, 2018.

Mullins, "Statistics for the Quality Control Chemistry Laboratory," 2003, Chapter I, pp. 10-17.

SNAC, Synchem, http://www.synchem.de/product/snac, accessed Aug. 16, 2018.

Valentino et al., "Current Trends in Targeting the Hormonal Regulation of Appetite and Energy Balance to Treat Obesity," Expert Rev Endocrinol Metab, 2010, vol. 5, pp. 765-783.

WHO Drug Information, "International Nonproprietary Names for Pharmaceutical Substances," 2009, vol. 23, No. 2, p. 164.

U.S. Appl. No. 61/425,087, filed Dec. 20, 2010.

EP Application No. 10195285.1, filed Dec. 16, 2010.

Anonymous, "Eligen@ Technology. Summary and Value Proposition", Emisphere, Feb. 24, 2017, pp. 1-10, URL: https://www.emisphere.com/wp-content/uploads/2017/02/Eligen-Technology-Presentation_2.15-Update.pdf, XP055520567.

Wang et al., "Non-peptidic glucose-like peptide-1 receptor agonists: aftermath of serendipitous discovery," Acta Pharmacol. Sinica, 2010, vol. 31, pp. 1026-1030.

(56) References Cited

OTHER PUBLICATIONS

Baynes, Kevin C. R., "The evolving world of GLP-1 agonist therapies for type 2 diabetes" Therapeutic Advances in Endocrinology and Metabolism, 2010, vol. 1, No. 2, pp. 61-67.

Buckley, Stephen T. et al., "Transcellular stomach absorption of a derivatized glucagon-like peptide-1 receptor agonist" Science Translational Medicine, Nov. 14, 2018, vol. 10, pp. 1-14.

Christensen, Mikkel et al., "Once-Weekly GLP-1 Agonists: How Do They Differ from Exenatide and Liraglutide?" Curr Diab Rep, 2010, vol. 10, pp. 124-132.

Davies, Melanie et al., "Effect of Oral Semaglutide Compared with Placebo and Subcutaneous Semaglutide on Glycemic Control in Patients with Type 2 Diabetes" JAMA, 2017, vol. 318, pp. 1460-1470.

Declaration by the Inventor, Flemming S. Nielsen, dated Feb. 11, 2019.

EMEA Assessment Report EMEA/379172/2009 for Victoza (liraglutide), 2009.

Goldberg, Michael et al., "Challenges for the Oral Delivery of Macromolecules" Nature Reviews Drug Discovery, 2003, vol. 2, pp. 289-294.

Granhall, Charlotte et al., "Safety and Pharmacokinetics of Single and Multiple Ascending Doses of the Novel Oral Human GLP-1 Analogue, Oral Semaglutide, in Healthy Subjects and Subjects with Type 2 Diabetes" Clinical Pharmacokinetics, published Dec. 18, 2018.

Hellriegel, Edward T. et al., "Interpatient variability in bioavailability is related to the extent of absorption: Implications for bioavailability and bioequivalence studies" Clinical Pharmacology & Therapeutics, Dec. 1996, vol. 60, No. 6, pp. 601-607.

King, Simon, "ViewPoints: Novo Nordisk R&D chief predicts an oral revolution for biologics" Nov. 14, 2018, Available from: [http://www.firstwordpharma.com/print/1604592?tsid=17].

Lee, Hye J., "Protein Drug Oral Delivery: The Recent Progress" Archives of Pharmacal Research, 2002, vol. 25, No. 5, pp. 572-584.

Madsen, Kjeld et al., "Structure—Activity and Protraction Relationship of Long-Acting Glucagon-like Peptide-1 Derivatives: Importance of Fatty Acid Lenght, Polarity, and Bulkiness" J. Med. Chem., 2007, vol. 50, pp. 6126-6132.

Morishita, Mariko et al., "Is the oral route possible for peptide and protein drug delivery?" Drug Discovery Today, Oct. 2006, vol. 11, No. 19/20, pp. 905-910.

Novo Nordisk Company announcement No. 14/2015, dated Feb. 20, 2015.

Novo Nordisk Company announcement No. 52/2015, dated Aug. 26, 2015.

Novo Nordisk Company announcement No. 17/2018, dated Feb. 22, 2018.

Novo Nordisk Company announcement No. 47/2018, dated May 29, 2018.

Novo Nordisk Company announcement No. 51/2018, dated Jun. 20, 2018.

Novo Nordisk Company announcement No. 53/2018, dated Jun. 28, 2018.

Novo Nordisk Company announcement No. 66/2018, dated Aug. 20, 2018.

Novo Nordisk Company announcement No. 74/2018, dated Sep. 20, 2018.

Novo Nordisk Company announcement No. 81/2018, dated Oct. 26, 2018.

Novo Nordisk Company announcement No. 89/2018, dated Nov. 22, 2018.

Novo Nordisk Company announcement No. 90/2018, dated Nov. 23, 2018.

Owens, D.R. et al., "Alternative routes of insulin delivery" Diabetic Medicine, 2003, vol. 20, pp. 886-898.

Thepharmaletter, "'8-10 years ahead' of field in oral delivery, senior execs say Novo is becoming a GLP-1 company" May 16, 2018, [cited Jan. 24, 2019] Available from: [https://www.thepharmaletter.com/article/8-10-years-ahead-of-field-in-oral-delivery-senior-execs-say-novo-nordisk-is-becoming-a-glp-1-company].

Matson, Estelle et al., "Population Pharmacokinetics of Liraglutide, a Once-Daily Human Glucagon-Like Peptide-1 Analog, in Healthy Volunteers and Subjects With Type 2 Diabetes, and Comparison to Twice-Daily Exenatide" J. Clin Pharmacology, 2010, vol. 50, pp. 886-894.

* cited by examiner

COMPOSITIONS COMPRISING A DELIVERY AGENT AND PREPARATION THEREOF

CROSS-REFERENCE TO RELATED APPLICATIONS

This application is a 35 U.S.C. § 371 National Stage application of International Application PCT/EP2013/055363 (WO 2013/139695), filed Mar. 15, 2013, which claimed priority of European Patent Application 12160742.8, filed Mar. 22, 2012 and priority of European Patent Application 13153422.4, filed Jan. 31, 2013; this application claims priority under 35 U.S.C. § 119 of U.S. Provisional Application 61/748,844; filed Jan. 4, 2013; the contents of which are incorporated by reference.

The present invention is directed to compositions comprising a delivery agent as well as processes for their preparation and use thereof in medicine.

In accordance with 37 C.F.R. § 1.52(e)(5), Applicants enclose herewith the Sequence Listing for the above-captioned application entitled "SEQUENCE LISTING", created on Mar. 15, 2013. The Sequence Listing is made up of 969 bytes, and the information contained in the attached "SEQUENCE LISTING" is identical to the information in the specification as originally filed. No new matter is added.

BACKGROUND

Pharmaceutical formulations comprising proteins and peptides can be manufactured from for example granules, which are compressed into tablets, or from blends of granules and excipient(s), which are compressed into tablets. The granulation process may be carried out as a dry granulation process where granules are formed from either blends containing excipients or from blends comprising the pharmaceutical active ingredient and one or more excipients. Dry granulation may be carried out by compaction of the blend into ribbons in a roller compactor followed by milling of the ribbons. A dry granulation process may also be carried out by compression of the blend into tablets followed by milling of the tablets, i.e. slugging.

In dry granulation processes, sticking of material to either the rolls of the roller compactor used for dry granulation or to the die and punches of the tablet press used to form granules/tablets may prevent proper processing resulting in an unacceptable product quality, i.e. granule quality or tablet quality, or in an unacceptable low process yield, or in no processability at all. In order to prevent such sticking, lubricant(s) are frequently added to the blend. Lubricants may comprise magnesium stearate, stearic acid, talc, etc. It is well-known that lubrication of the blend used for dry granulation is a major cause of decreased mechanical strength and prolonged disintegration time of the final compressed tablets. Likewise lubrication of the blend for tablet compression is well known to reduce the mechanical strength of the tablets, prolong the disintegration time of the tablets, prolong the release of the pharmaceutical active ingredient from the tablet and increase tablet friability. This phenomenon is known as over-lubrication.

Over-lubrication is caused by high concentration of lubricant(s) or by long mixing time of the lubricant(s) with the remaining ingredients of the blend used for either dry granulation or tablet compression. Over-lubrication may be caused by formation of a hydrophobic layer around powders and/or granules used to manufacture the tablet leading to e.g. slower dissolution and/or poorer wetting and/or reduced binding properties. Therefore, the mixing time of the lubricant(s) has to be carefully controlled and kept at a minimum, while keeping the concentration of lubricant(s) as low as possible to prevent the undesirable effects of over-lubrication.

SUMMARY

In some embodiments the invention relates to a granule comprising a salt of N-(8-(2-hydroxybenzoyl)amino) caprylic acid and a lubricant, wherein the composition is obtained by mixing said salt of N-(8-(2-hydroxybenzoyl) amino)caprylic and said lubricant for more than 5 minutes prior to granulation.

In some embodiments the invention relates to a process of producing a pharmaceutical composition comprising granules comprising a salt of N-(8-(2-hydroxybenzoyl)amino) caprylic acid and a lubricant, such a magnesium stearate, wherein said process comprises the steps: a) mixing said salt of N-(8-(2-hydroxybenzoyl)amino)caprylic acid and said lubricant for more than 5 minutes; and b) optionally roller compacting the mixture of step a.

In some embodiments the invention relates to a pharmaceutical composition obtained by the process as defined herein. In some embodiments the invention relates to a granule obtained by the process as defined herein.

In some embodiments the invention relates to a composition or a granule as defined herein for use in medicine, such as for treatment of diabetes or obesity. In some embodiments the invention relates to a method for treatment of diabetes or obesity comprising administering the composition or a granule as defined herein.

DESCRIPTION

In some embodiments the present invention relates to tablets prepared from a blend of granules and excipients. In some embodiments the term "granule" refers to particles gathered into larger particles. In some embodiments a "granule" is formed by gathering small particles into a large mass. In some embodiments the term "granulate" refers to several granules, such as two or more granules. The granules, which comprise a substance that promotes the absorption of drugs, were prepared by roller compaction using a high concentration of the lubricant magnesium stearate, i.e. 2 to 5% (w/w). The present inventors surprisingly found that the mixing time of the lubricant/excipient blend for the granules, which was used for the dry granulation process, had no disadvantageous effect in terms of reduced mechanical strength of the tablets, prolonged disintegration time of the tablets or increased tablet friability. Contrary to common general knowledge no or even a beneficial impact of the mixing time of the lubricant/excipient blend for the granules on the pharmaceutical technical properties of the tablets were seen, i.e. unaltered or higher crushing strength and unaltered or lower friability of the final tablets was obtained.

Likewise, the size of the granules and the extent of granulation were surprisingly unaffected by changes in the mixing time of the lubricant/excipient blend for the granules.

Accordingly, in some embodiments the present invention provides a larger window of time in which the mixing step of the lubricant/excipient blend for the granules can be performed in the manufacture of tablets without detrimental effects on the tablet properties, such as mechanical strength and/or friability.

Pharmaceutical Compositions

In some embodiments the invention relates to a granule comprising a salt of N-(8-(2-hydroxybenzoyl)amino)caprylic acid and a lubricant, wherein the composition is obtained by mixing said salt of N-(8-(2-hydroxybenzoyl)amino)caprylic and said lubricant for more than 5 minutes prior to granulation. In some embodiments the invention relates to a pharmaceutical composition comprising a salt of N-(8-(2-hydroxybenzoyl)amino)caprylic acid and a lubricant, wherein the composition is obtained by mixing said salt of N-(8-(2-hydroxybenzoyl)amino)caprylic and said lubricant for more than 5 minutes.

In some embodiments the duration of said mixing is at least 6 minutes, such as at least 7, 8, 9, 10, 11, 12, 13, 14, 15, 16, 17, 18, 19, 20, 21, 22, 23, 24, 25, 26, 27, 28, 29, 30, 35, 40, 45 or 50 minutes. In some embodiments the duration of said mixing is at least 30 minutes or at least 40 minutes, such as at least 50 minutes. In some embodiments the duration of said mixing is no more than 12 hours, such as no more than 10, 8, 6, 4, or 2 hours.

In some embodiments the amount of lubricant is at least 0.25% (w/w) or at least 0.5% (w/w), such as at least 1% (w/w) or at least 2% (w/w), of said composition. In some embodiments the amount of lubricant is no more than 10% (w/w), such as no more than 8, 7, or 6% (w/w), of said composition. In some embodiments the lubricant is magnesium stearate.

In some embodiments the composition comprises one or more pharmaceutically acceptable excipients. In some embodiments the composition comprises a filler, such as microcrystalline cellulose. In some embodiments the composition comprises a binder, such as povidone. As used herein the term "composition" refers to a pharmaceutical composition.

In some embodiments the composition comprises granules which have been manufactured by dry granulation. In some embodiments the composition comprises granules which have been manufactured by roller compaction. In some embodiments the moldings from the roller compactions process are comminuted into granules.

In some embodiments the composition is in the form of a solid dosage form. In some embodiments the composition is in the form of a tablet. In some embodiments the composition is in the form of a capsule. In some embodiments the composition is in the form of a sachet.

In some embodiments the composition or granule comprises at least one pharmaceutically acceptable excipient. The term "excipient" as used herein broadly refers to any component other than the active therapeutic ingredient(s). The excipient may be an inert substance, which is inert in the sense that it substantially does not have any therapeutic and/or prophylactic effect per se. The excipient may serve various purposes, e.g. as a delivery agent, absorption enhancer, vehicle, filler (also known as diluents), binder, lubricant, glidant, disintegrant, crystallization retarders, acidifying agent, alkalizing agent, preservative, antioxidant, buffering agent, chelating agent, complexing agents, surfactant agent, emulsifying and/or solubilizing agents, sweetening agents, wetting agents stabilizing agent, colouring agent, flavouring agent, and/or to improve administration, and/or absorption of the active substance. A person skilled in the art may select one or more of the aforementioned excipients with respect to the particular desired properties of the solid oral dosage form by routine experimentation and without any undue burden. The amount of each excipient used may vary within ranges conventional in the art. Techniques and excipients which may be used to formulate oral dosage forms are described in Handbook of Pharmaceutical Excipients, 6th edition, Rowe et al., Eds., American Pharmaceuticals Association and the Pharmaceutical Press, publications department of the Royal Pharmaceutical Society of Great Britain (2009); and Remington: the Science and Practice of Pharmacy, 21th edition, Gennaro, Ed., Lippincott Williams & Wilkins (2005).

In some embodiments the composition or granule comprises a filler, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), other cellulose derivatives, sucrose, sorbitol, mannitol, dextrins, dextrans, maltodextrins, dextrose, fructose, kaolin, mannitol, sorbitol, sucrose, sugar, starches or modified starches (including potato starch, maize starch and rice starch), calcium phosphate (e.g. basic calcium phosphate, calcium hydrogen phosphate, dicalcium phosphate hydrate), calcium sulphate, calcium carbonate, or sodium alginate. In some embodiments the filler is microcrystalline cellulose, such as Avicel PH 101.

In some embodiments the composition or granule comprises a binder, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), hydroxypropylcellulose, L-hydroxypropylcellulose (low-substituted), hypromellose (HPMC) (e.g. Methocel E, F and K, Metolose SH of Shin-Etsu, Ltd, such as, e.g., the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, ethylcellulose, sodium carboxymethylcellulose, other cellulose derivatives, sucrose, dextrins, maltodextrins, starches or modified starches (including potato starch, maize starch and rice starch), calcium lactate, calcium carbonate, acacia, sodium alginate, agar, carrageenan, gelatin, guar gum, pectin, PEG, or povidone. In some embodiments the binder is povidone, such as Povidone K 90.

In some embodiments the composition or granule comprises a disintegrant, such as alginic acid, alginates, microcrystalline cellulose, hydroxypropyl cellulose, other cellulose derivatives, croscarmellose sodium, crospovidone, polacrillin potassium, sodium starch glycolate, starch, pregelatinized starch, or carboxymethyl starch (e.g. Primogel® and Explotab®).

In some embodiments the composition or granule comprises a lubricant, such as stearic acid, magnesium stearate, calcium stearate or other metallic stearate, talc, waxes, glycerides, light mineral oil, glycerylbehenate, hydrogenated vegetable oils, sodium stearylfumarate, polyethylene glycols, alkyl sulfates, or sodium benzoate. In some embodiments the composition or granule comprises a lubricant, such as magnesium silicate, talc, or colloidal silica. In some embodiments the lubricant is magnesium stearate.

In some embodiments the composition or granule comprises one or more excipients selected from crystallization retarders, such as Povidone, etc.; solubilizing agents (also known as surfactants), such as anionic surfactants (e.g. Pluronic or Povidone), cationic surfactants, nonionic surfactants, and/or zwitterionic surfactants; colouring agents, including dyes and pigments, such as Iron Oxide Red or Yellow, titanium dioxide, and/or talc; and/or pH control agents, such as citric acid, tartaric acid, fumaric acid, sodium citrate, dibasic calcium phosphate, and/or dibasic sodium phosphate.

In some embodiments the composition comprises one or more pharmaceutically acceptable excipients. In some embodiments the composition comprises a filler and/or a binder. In some embodiments the filler is microcrystalline cellulose. In some embodiments the binder is povidone. In some embodiments the composition comprises a lubricant. In some embodiments the lubricant is magnesium stearate.

In some embodiments the composition comprises at least 60% (w/w) delivery agent, less than 10% (w/w) binder, 5-40% (w/w) filler, and less than 10% (w/w) lubricant.

In some embodiments the composition comprises at least 60% (w/w), such as 65-75% (w/w), 60-80% (w/w), or 50-90% (w/w), delivery agent. In some embodiments the composition comprises at least 70% (w/w), such as 70-80% (w/w), delivery agent.

In some embodiments the composition comprises 0.1-10% (w/w), such as 0.2-4% (w/w) or 0.5-3% (w/w), binder. In some embodiments the composition comprises 1.5-2.5% (w/w), such as 1.7-2.3% (w/w), 1.8-2.2% (w/w), or 1.9-2.1% (w/w), binder. In some embodiments the composition comprises 1% (w/w) or 2% (w/w) binder.

In some embodiments the composition comprises 5-40% (w/w), such as 10-30% (w/w) or 5-25% (w/w), filler. In some embodiments the composition comprises 10-25% (w/w), such as 17-23% (w/w), 18-22% (w/w), or 19-21% (w/w), filler. In some embodiments the composition comprises 10.9% (w/w) or 18% (w/w) filler, or comprises 19.5% (w/w) or 20.5% (w/w) filler.

In some embodiments the composition comprises 0.1-10% (w/w) or 0.5-5% (w/w), such as 1-3.5% (w/w) or 1% (w/w), lubricant. In some embodiments the composition comprises 1.5-3% (w/w), such as 2.1-2.7% (w/w), 2.2-2.6% (w/w) or 2.3-2.5% (w/w), lubricant.

Still further, the composition or granule of the invention may be formulated as is known in the art of oral formulations of insulinotropic compounds.

In some embodiments the invention relates to a pharmaceutical composition comprising a first and a second type of granules. In some embodiments the pharmaceutical composition further comprises an extragranular lubricant, such as magnesium stearate.

In some embodiments the invention relates to a first granule comprising at least 75% (w/w) delivery agent, less than 10% (w/w) lubricant, and optionally less than 20% filler and no GLP-1 peptide. In some embodiments the invention relates to a first granule comprising at least 80% (w/w) delivery agent, less than 10% (w/w) lubricant, and optionally less than 20% filler and no GLP-1 peptide. In some embodiments the first granule comprises 75-90% (w/w), such as 78-88% (w/w), 80-86% (w/w) or 82-84% (w/w), delivery agent. In some embodiments the first granule comprises less than 10% (w/w), such as 1-3% (w/w), 1.5-2.5% (w/w) or 1.9-2.3% (w/w), lubricant, In some embodiments the first granule comprises less than 20%, such as 10-20% (w/w), 12-18% (w/w) or 14-17% (w/w), filler. In some embodiments the first granule comprises no GLP-1 peptide. In some embodiments the granule comprises at least 80% (w/w) delivery agent, less than 10% (w/w) lubricant, and optionally less than 20% filler.

In some embodiments the invention relates to a second granule comprising a GLP-1 peptide, at least 15% (w/w) filler and less than 40% (w/w) binder and no salt of NAC. In some embodiments the second granule comprises at least 1%, such as 1-70% (w/w), 2-40% (w/w) or 4-30% (w/w), GLP-1 peptide. In some embodiments the second granule comprises at least 20%, such as 40-80% (w/w) or 50-75% (w/w), filler. In some embodiments the second granule comprises less than 30%, such as 5-30% (w/w), 10-28% (w/w) or 15-25% (w/w), binder. In some embodiments the second granule comprises no salt of NAC. In some embodiments the granule comprises a GLP-1 peptide, at least 15% (w/w) filler and less than 40% (w/w) binder. In some embodiments the granule comprises at least 60% (w/w) filler and less than 40% (w/w) binder. The composition or granule may be administered in several dosage forms, for example as a tablet; a capsule such as hard capsules, sachet or a powder. The composition or granule may further be compounded in a drug carrier or drug delivery system, e.g. in order to improve stability and/or solubility or further improve bioavailability. In some embodiments the composition is in the form of a solid dosage form. In some embodiments the solid dosage form is a tablet. In some embodiments the composition is in the form of a capsule. In some embodiments the composition is in the form of a sachet.

In some embodiments the weight of the tablet is in the range of 150 mg to 1000 mg, such as in the range of 300-600 mg or 350-450 mg.

Methods of Preparation of Pharmaceutical Compositions

The composition of the invention may be prepared as is known in the art. In some embodiments the composition or the granule may be prepared as described in the examples herein. In some embodiments the composition may be granulated prior to being compressed into tablets. In some embodiments the granules of the invention are manufactured by dry granulation, such as by roller compaction. In some embodiments the moldings from the roller compactions process are comminuted into granules. The composition may comprise one or more intragranular parts and an extragranular part, wherein the intragranular parts have been granulated, and wherein the extragranular part has been added after granulation. A first intragranular part may comprise the GLP-1 peptide and one or more excipients, and a second intragranular part may comprise the delivery agent and optionally one or more excipients. A first intragranular part may comprise the GLP-1 peptide, filler and/or a binder and a second intragranular part may comprise the delivery agent, lubricant and/or filler. In some embodiments the first intragranular part comprises the GLP-1 agonist (i.e. the GLP-1 peptide), microcrystalline cellulose and/or povidone and the second intragranular part comprises the delivery agent, magnesium stearate and/or microcrystalline cellulose. The extragranular part may comprise a lubricant. In some embodiments the extragranular part comprises magnesium stearate. In some embodiments the filler and/or a binder is a filler or and filler and a binder.

To prepare a dry blend of tabletting material, the various components are weighed, optionally delumped and then combined. The mixing of the components may be carried out until a homogeneous blend is obtained.

If granules are to be used in the tabletting material, granules may be produced in a manner known to a person skilled in the art, for example by dry granulation techniques in which the pharmaceutically active agent and/or delivery agents are compacted with the excipients to form relatively large moldings, for example slugs or ribbons, which are comminuted by grinding, and the ground material serves as the tabletting material to be later compressed into tablets. Suitable equipment for dry granulation includes but is not limited to roller compaction equipment from Gerteis, such as Gerteis MINI-PACTOR.

To compress the tabletting material into a solid oral dosage form, for example a tablet, a tablet press may be used. In a tabletting press, the tabletting material is filled (e.g. force fed or gravity fed) into a die cavity. The tabletting material is then compressed by a punch with pressure. Subsequently, the resulting compact, or tablet is ejected from the tabletting press. The above mentioned compression process is subsequently referred to herein as the "compression process". Suitable tablet presses include, but are not limited to, rotary tablet presses and eccentric tablet presses. Examples of tablet presses include, but are not limited to, the Fette 102i (Fette GmbH), the Korsch XL100, the Korsch PH 106 rotary tablet press (Korsch AG, Germany), the Korsch EK-O eccentric tabletting press (Korsch AG, Germany) and the Manesty F-Press (Manesty Machines Ltd., United Kingdom).

In some embodiments the method of preparation of the tablet comprises i) dry granulation of a mixture comprising the GLP-1 agonist (i.e. the GLP-1 peptide), filler and a binder; ii) dry granulation of a mixture comprising the delivery agent, lubricant and/or filler iii) mixing of the granules with a lubricant, and then iv) compression of the blend into tablets.

In some embodiments the invention relates to a process of producing a pharmaceutical composition comprising granules comprising a salt of N-(8-(2-hydroxybenzoyl)amino) caprylic acid and a lubricant, such a magnesium stearate, wherein said process comprises the steps: a) mixing said salt of N-(8-(2-hydroxybenzoyl)amino)caprylic acid and said lubricant for more than 5 minutes; and b) optionally roller compacting the mixture of step a. In some embodiments the invention relates to a process of producing a pharmaceutical composition comprising a salt of N-(8-(2-hydroxybenzoyl) amino)caprylic acid and a lubricant, such as magnesium stearate, wherein said process comprises the steps: a) mixing said salt of N-(8-(2-hydroxybenzoyl)amino)caprylic acid and said lubricant for more than 5 minutes; and b) optionally roller compacting the mixture of step a. In some embodiments the mixing in step a is at least 6 minutes, such as at least 7, 8, 9, 10, 11, 12, 13, 14, 15, 16, 17, 18, 19, 20, 21, 22, 23, 24, 25, 26, 27, 28, 29, 30, 35, 40, 45 or 50 minutes. In some embodiments the mixing in step a is at least 10 minutes or at least 20 minutes. In some embodiments the mixing in step a is at least 30 minutes or at least 40 minutes, such as at least 50 minutes. In some embodiments the mixing in step a is in the range of from 6 minutes to 12 hours, such as from 10 minutes to 10 hours or from 15 minutes to 8 hours. In some embodiments the duration of said mixing in step a is no more than 12 hours, such as no more than 10, 8, 6, 4, or 2 hours. In some embodiments the amount of lubricant is at least 0.25% (w/w) or at least 0.5% (w/w), such as at least 1% (w/w) or at least 2% (w/w), of said composition. In some embodiments the amount of lubricant is no more than 10% (w/w), such as no more than 8, 7, or 6% (w/w), of said composition.

In some embodiments the invention relates to a composition or a granule obtained by the process as defined herein.

In some embodiments dry granulation is carried out by roller compaction.

In some embodiments the term "resistance to crushing of tablets" has the meaning defined in section 2.9.8 in the European Pharmacopoeia 7.5, 7th edition 2012; resistance to crushing may be measured inter alia in Newton (N) or kilopond (kP) using a jaw speed of 20 N/s (1 kP equals 9.807 N).

In some embodiments the term "friability" has the meaning defined in section 2.9.7 in the European Pharmacopoeia 7.5, 7th edition 2012.

In some embodiments the term "particle size" means the volume distribution of equivalent spherical diameters as determined by laser diffraction at 3 bar dispersive pressure and at a obscuration in the range from 0.05-8% in a Malvern Mastersizer 2000 Scirocco 2000 (dry mode) using general purpose enhanced sensitivity (Mie approximation) and a refractive index of 1.65.

In some embodiments the term "disintegration time" has the meaning defined in section 2.9.1 in the European Pharmacopoeia 7.5, 7th edition 2012 and the liquid medium used for the disintegration test is water-R as defined in the European Pharmacopoeia 7.5, 7th edition 2012.

In some embodiments the term "compression force" means the force exerted between the upper and lower punches when compressing materials into a tablet as determined by a load cell transducer that converts the force into electrical signal using a strain gauge; the compression force may be measured inter alia in Newton (N) or kilopond (kP) (1 kP equals 9.807 N).

In some embodiments the term "roller compaction force" means the force exerted between the rolls of the roller compactor when compacting materials into a continuous strip of compressed material as determined by a pressure transducer that converts the hydraulic pressure into electrical signal; the roller compaction force may be measured in kiloNewton (kN) or in kiloNewton per roll width (kN/cm).

Salt of N-(8-(2-hydroxybenzoyl)amino)caprylic acid

The delivery agent used in the present invention is a salt of N-(8-(2-hydroxybenzoyl)amino)caprylic acid. In some embodiments the delivery agent is an absorption enhancer. The structural formula of N-(8-(2-hydroxybenzoyl)amino) caprylate is shown in formula (I).

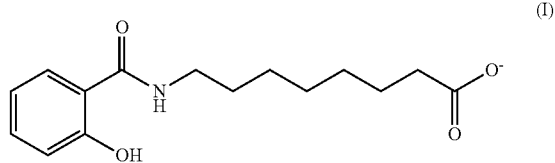 [SMILES: O=C([O-])CCCCCCCNC(=O)c1ccccc1O]

In some embodiments the salt of N-(8-(2-hydroxybenzoyl)amino)caprylic acid is in the caprylic acid form and/or the caprylate form. In some embodiments the salt of N-(8-(2-hydroxybenzoyl)amino)caprylic acid comprises one monovalent cation, two monovalent cations or one divalent cation. In some embodiments the salt of N-(8-(2-hydroxybenzoyl)amino)caprylic acid is selected from the group consisting of the sodium salt, potassium salt and calcium salt of N-(8-(2-hydroxybenzoyl)amino)caprylic acid.

Salts of N-(8-(2-hydroxybenzoyl)amino)caprylate may be prepared using the method described in e.g. WO96/030036, WO00/046182, WO01/092206 or WO2008/028859.

The salt of N-(8-(2-hydroxybenzoyl)amino)caprylic acid may be crystalline and/or amorphous. In some embodiments the delivery agent comprises the anhydrate, monohydrate, dihydrate, trihydrate, a solvate or one third of a hydrate of the salt of N-(8-(2-hydroxybenzoyl)amino) caprylic acid as well as combinations thereof. In some embodiments the delivery agent is a salt of N-(8-(2-hydroxybenzoyl)amino)

caprylic acid as described in WO2007/121318. The salt of N-(8-(2-hydroxybenzoyl)amino)caprylic acid may be any polymorph thereof.

In some embodiments the delivery agent is sodium N-(8-(2-hydroxybenzoyl)amino)caprylate (referred to as "SNAC" herein), also known as sodium 8-(salicyloylamino) octanoate.

In some embodiments the amount of the salt of N-(8-(2-hydroxybenzoyl)amino)caprylic acid in the composition is in the range of 0.6-3.5 mmol. In some embodiments the amount of the salt of N-(8-(2-hydroxybenzoyl)amino) caprylic acid in the composition is at least 0.6 mmol, such as selected from the group at least 0.8 mmol or at least 0.9 mmol. In some embodiments the amount of the salt of N-(8-(2-hydroxybenzoyl)amino)caprylic acid in the composition is up to 2.5 mmol. In some embodiments the amount of the salt of N-(8-(2-hydroxybenzoyl)amino)caprylic acid in the composition is 0.6-2.0 mmol. In some embodiments the amount of the salt of N-(8-(2-hydroxybenzoyl)amino) caprylic acid is 1 mmol, such as 1.08 mmol.

In some embodiments the amount of SNAC in the composition is in the range of 100-1000 mg. In some embodiments the amount of SNAC in the composition is at least 150 mg or at least 250 mg. In some embodiments the amount of SNAC in the composition is up to 800 mg, such as up to 700 mg or up to 600 mg. In some embodiments the amount of SNAC in the composition is 300 mg.

In some embodiments the molar ratio between GLP-1 agonist (i.e. the GLP-1 peptide) and delivery agent in the composition is less than 10, such as less than 5 or less than 1. In some embodiments the molar ratio between GLP-1 agonist (i.e. the GLP-1 peptide) and delivery agent in the composition is less than 1/10, such as less than 1/100 or less than 5/1000.

Pharmaceutically Active Agents

In some embodiments the composition of the invention comprises a pharmaceutically active agent, such as a peptide or a protein. In some embodiments said pharmaceutically active agent is a GLP-1 peptide. In some embodiments the GLP-1 peptide is referred to as a GLP-1 agonist.

The term "GLP-1 peptide" as used herein refers to a compound, which fully or partially activates the human GLP-1 receptor. In some embodiments the "GLP-1 peptide" binds to a GLP-1 receptor, e.g., with an affinity constant ($K_D$) or activate the receptor with a potency ($EC_{50}$) of below 1 µM, e.g. below 100 nM as measured by methods known in the art (see e.g. WO 98/08871) and exhibits insulinotropic activity, where insulinotropic activity may be measured in vivo or in vitro assays known to those of ordinary skill in the art. For example, the GLP-1 peptide may be administered to an animal with increased blood glucose (e.g. obtained using an Intravenous Glucose Tolerance Test (IVGTT), a person skilled in the art will be able to determine a suitable glucose dosage and a suitable blood sampling regime, e.g. depending on the species of the animal, for the IVGTT) and the plasma insulin concentration measured over time.

In some embodiments the GLP-1 peptide is a GLP-1 analogue, optionally comprising one substituent. The term "analogue" as used herein referring to a GLP-1 peptide (hereafter "peptide") means a peptide wherein at least one amino acid residue of the peptide has been substituted with another amino acid residue and/or wherein at least one amino acid residue has been deleted from the peptide and/or wherein at least one amino acid residue has been added to the peptide and/or wherein at least one amino acid residue of the peptide has been modified. Such addition or deletion of amino acid residues may take place at the N-terminal of the peptide and/or at the C-terminal of the peptide. In some embodiments a simple nomenclature is used to describe the GLP-1 peptide, e.g., [Aib8] GLP-1(7-37) designates an analogue of GLP-1(7-37) wherein the naturally occurring Ala in position 8 has been substituted with Aib. In some embodiments the GLP-1 peptide comprises a maximum of twelve, such as a maximum of 10, 8 or 6, amino acids which have been altered, e.g., by substitution, deletion, insertion and/or modification, compared to e.g. GLP-1(7-37). In some embodiments the analogue comprises up to 10 substitutions, deletions, additions and/or insertions, such as up to 9 substitutions, deletions, additions and/or insertions, up to 8 substitutions, deletions, additions and/or insertions, up to 7 substitutions, deletions, additions and/or insertions, up to 6 substitutions, deletions, additions and/or insertions, up to 5 substitutions, deletions, additions and/or insertions, up to 4 substitutions, deletions, additions and/or insertions or up to 3 substitutions, deletions, additions and/or insertions, compared to e.g. GLP-1(7-37). Unless otherwise stated the GLP-1 comprises only L-amino acids.

In some embodiments the term "GLP-1 analogue" or "analogue of GLP-1" as used herein refers to a peptide, or a compound, which is a variant of the human Glucagon-Like Peptide-1 (GLP-1(7-37)). GLP-1(7-37) has the sequence HAEGTFTSDV SSYLEGQAAKEFIAWLVKGRG (SEQ ID No: 1). In some embodiments the term "variant" refers to a compound which comprises one or more amino acid substitutions, deletions, additions and/or insertions.

In some embodiments the GLP-1 peptide exhibits at least 60%, 65%, 70%, 80% or 90% sequence identity to GLP-1 (7-37) over the entire length of GLP-1(7-37). As an example of a method for determination of sequence identity between two analogues the two peptides [Aib8]GLP-1(7-37) and GLP-1(7-37) are aligned. The sequence identity of [Aib8] GLP-1(7-37) relative to GLP-1(7-37) is given by the number of aligned identical residues minus the number of different residues divided by the total number of residues in GLP-1 (7-37). Accordingly, in said example the sequence identity is (31-1)/31.

In some embodiments the C-terminal of the GLP-1 peptide is an amide.

In some embodiments the GLP-1 peptide is GLP-1(7-37) or GLP-1(7-36)amide. In some embodiments the GLP-1 peptide is exendin-4, the sequence of which is HGEGTFITSDLSKQMEEEAVRLFIEWLKNGGPSSGAPPPS (SEQ ID No: 2).

In some embodiments the GLP-1 peptide comprises one substituent which is covalently attached to the peptide. In some embodiments the substituent comprises a fatty acid or a fatty diacid. In some embodiments the substituent comprises a C16, C18 or C20 fatty acid. In some embodiments the substituent comprises a C16, C18 or C20 fatty diacid. In some embodiments the substituent comprises formula (X)

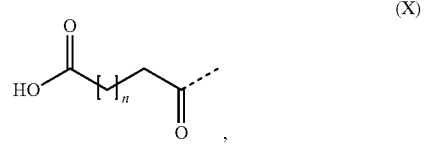

wherein n is at least 13, such as n is 13, 14, 15, 16, 17, 18 or 19. In some embodiments the substituent comprises formula (X), wherein n is in the range of 13 to 19, such as in the range of 13 to 17. In some embodiments the substituent comprises formula (X), wherein n is 13, 15 or 17. In some embodiments the substituent comprises formula (X), wherein n is 13. In some embodiments the substituent comprises formula (X), wherein n is 15. In some embodiments the substituent comprises formula (X), wherein n is 17. In some embodiments the substituent comprises one or more 8-amino-3,6-dioxaoctanoic acid (OEG), such as two OEG.

In some embodiments the substituent is [2-(2-{2-[2-(2-{2-[(S)-4-carboxy-4-(17-carboxyheptadecanoylamino)butyrylamino]ethoxy}ethoxy)acetylamino]ethoxy}ethoxy)acetyl].

In some embodiments the substituent is [2-(2-{2-[2-(2-{2-[(S)-4-carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl].

In some embodiments the GLP-1 peptide is semaglutide, also known as N-epsilon 26-[2-(2-{2-[2-(2-{2-[(S)-4-carboxy-4-(17-carboxyheptadecanoylamino) butyrylamino]ethoxy}ethoxy)acetylamino]ethoxy}ethoxy)acetyl][Aib8,Arg34]GLP-1(7-37), which may be prepared as described in WO2006/097537, Example 4.

In some embodiments the composition comprises the GLP-1 peptide or a pharmaceutically acceptable salt, amide, or ester thereof. In some embodiments the composition comprises the GLP-1 peptide one or more pharmaceutically acceptable counter ions.

In some embodiments the dosage of GLP-1 peptide is in the range of 0.01 mg to 100 mg. In some embodiments the composition comprises an amount of a GLP-1 peptide in the range of 1 to 80 mg or 5 to 60 mg. In some embodiments the composition comprises an amount of a GLP-1 peptide of 5 mg, such as 10 mg or 60 mg.

In some embodiments the composition comprises an amount of a GLP-1 peptide in the range of 0.05 to 25 µmol, such as in the range of 0.5 to 20 µmol.

In some embodiments the GLP-1 peptide is selected from one or more of the GLP-1 peptides mentioned in WO93/19175, WO96/29342, WO98/08871, WO99/43707, WO99/43706, WO99/43341, WO99/43708, WO2005/027978, WO2005/058954, WO2005/058958, WO2006/005667, WO2006/037810, WO2006/037811, WO2006/097537, WO2006/097538, WO2008/023050, WO2009/030738, WO2009/030771 and WO2009/030774.

In some embodiments the GLP-1 peptide is selected from the group consisting of N-epsilon37{2-[2-(2-{2-[2-((R)-3-carboxy-3-{[1-(19-carboxynonadecanoyl) piperidine-4-carbonyl]amino}propionylamino)ethoxy]ethoxy}acetylamino)ethoxy]ethoxy}acetyl [desaminoHis7,Glu22,Arg26,Arg34,Lys37]GLP-1(7-37)amide; N-epsilon26{2-[2-(2-{2-[2-((R)-3-carboxy-3-{[1-(19-carboxynonadecanoyl) piperidine-4-carbonyl]amino}propionylamino)ethoxy]ethoxy}acetylamino)ethoxy]ethoxy}acetyl [desaminoHis7,Arg34] GLP-1-(7-37); N-epsilon37{2-[2-(2-{2-[2-((S)-3-carboxy-3-{[1-(19-carboxy-nonadecanoyl) piperidine-4-carbonyl]amino}propionylamino)ethoxy]ethoxy}acetylamino)ethoxy]ethoxy}acetyl[Aib8,Glu22,Arg26,Arg34,Lys37]GLP-1-(7-37)amide; N-epsilon37-[2-(2-[2-(2-[2-((R)-3-[1-(17-carboxyheptadecanoyl)piperidin-4-ylcarbonylamino]3-carboxypropionylamino)ethoxy)ethoxy]acetylamino)ethoxy]ethoxy)acetyl][,DesaminoHis7, Glu22 Arg26, Arg 34, Phe(m-CF3)28]GLP-1-(7-37)amide; N-epsilon26-[(S)-4-carboxy-4-({trans-4-[(19-carboxynonadecanoylamino)methyl]cyclohexanecarbonyl}amino)butyryl][Aib8,Arg34]GLP-1-(7-37); N-epsilon26-{4-[(S)-4-carboxy-4-({trans-4-[(19-carboxynonadecanoylamino) methyl] cyclohexanecarbonyl}amino)butyrylamino]butyryl}[Aib8,Arg34]GLP-1-(7-37); N-epsilon26-[2-(2-{2-[(S)-4-carboxy-4-({trans-4-[(19-carboxy-nonadecanoylamino)methyl]cyclohexanecarbonyl}amino)butyrylamino]ethoxy}ethoxy)acetyl][Aib8,Arg34]GLP-1-(7-37); N-epsilon26-[2-(2-{2-[2-(2-{2-[(S)-4-carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][Aib8,Arg34]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino) butyrylamino]ethoxy}ethoxy)acetylamino]ethoxy}ethoxy)acetyl][Aib8,Glu22,Arg26, Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino) butyrylamino]ethoxy}ethoxy)acetylamino]ethoxy}ethoxy)acetyl][DesaminoHis7,Glu22,Arg26,Arg34,Lys37]GLP-1-(7-37)amide; N-epsilon37-[2-(2-{2-[2-(2-{2-[(S)-4-carboxy-4-({4-[(trans-19-carboxy-nonadecanoylamino)methyl]cyclohexanecarbonyl}amino) butyrylamino]ethoxy}ethoxy)acetylamino]ethoxy}ethoxy)acetyl][DesaminoHis7,Arg26,Arg34,Lys37]GLP-1-(7-37) amide; N-epsilon37-[2-(2-{2-[2-(2-{2-[(S)-4-carboxy-4-({trans-4-[(19-carboxy-nonadecanoylamino)methyl]cyclohexanecarbonyl}amino) butyrylamino]ethoxy}ethoxy)acetylamino]ethoxy}ethoxy)acetyl][DesaminoHis7,Glu22,Arg26,Arg34,Lys37]GLP-1-(7-37); N-epsilon26[2-(2-{2-[2-(2-{2-[(S)-4-carboxy-4-({4-[(19-carboxy-nonadecanoylamino)methyl]cyclohexanecarbonyl}amino) butyrylamino]ethoxy}ethoxy) acetylamino]ethoxy}ethoxy)acetyl[Aib8, Lys 26]GLP-1 (7-37)amide; N-epsilon26 [2-(2-[2-(2-[2-(-(S)-2-[trans-4-((9-carboxynonadecanoylamino]methyl) cyclohexylcarbonylamino]-4-carboxybutanoylamino) ethoxy)ethoxy]acetylamino)ethoxy]ethoxy)acetyl][Aib8, Lys26] GLP-1 (7-37)amide; N-epsilon37-[2-(2-{2-[2-(2-{2-[(S)-4-carboxy-4-({trans-4-[(19-carboxy-nonadecanoylamino)methyl]cyclohexane-carbonyl}amino)butyrylamino]ethoxy}ethoxy)acetylamino]ethoxy}ethoxy)acetyl] [DesaminoHis7,Arg26,Arg34,Lys37]GLP-1-(7-37); N-epsilon37-[2-(2-{2-[2-(2-{2-[(S)-4-carboxy-4-({trans-4-[(19-carboxy-nonadecanoylamino)methyl]cyclohexanecarbonyl}amino)butyrylamino]ethoxy}ethoxy)acetyl][DesaminoHis7,Glu22,Arg26,Glu30,Arg34,Lys37]GLP-1-(7-37); N-epsilon26-[2-(2-{2-[(S)-4-carboxy-4-((S)-4-carboxy-4-{4-[4-(16-(1H-tetrazol-5-yl)-hexadecanoylsulfamoyl)butyrylamino]-butyrylamino}butyrylamino)butyrylamino]ethoxy}ethoxy) acetyl][Aib8,Arg34]GLP-1-(7-37); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyrylamino) butyrylamino]ethoxy}ethoxy)acetyl][Aib8,Arg34]GLP-1-(7-37); N-epsilon26-[2-(2-{2-[(S)-4-carboxy-4-((S)-4-carboxy-4-{6-[4-(16-(1H-tetrazol-5-yl)hexadecanoyl-sulfamoyl)butyrylamino]hexanoylamino}butyrylamino)butyrylamino] ethoxy}ethoxy) acetyl][Aib8,Arg34]GLP-1-(7-37); N-epsilon26-[2-(2-{2-[(S)-4-carboxy-4-((S)-4-carboxy-4-{4-[4-(16-(1H-tetrazol-5-yl)hexadecanoylsulfamoyl)butyrylamino]butyrylamino}butyrylamino)butyrylamino] ethoxy}ethoxy)acetyl][Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]-dodecanoylamino}butyrylamino) butyrylamino]ethoxy}ethoxy)acetyl][Aib8,Arg34]GLP-1-(7-34); N-epsilon26-[2-(2-{2-[(S)-4-carboxy-4-((S)-4-carboxy-4-

{6-[4-(16-(1H-tetrazol-5-yl)hexadecanoylsulfamoyl)butyrylamino]hexanoylamino}butyrylamino) butyrylamino]ethoxy}ethoxy)acetyl][Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyrylamino)butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]hexanoylamino}butyrylamino)butyrylamino]ethoxy}ethoxy)acetyl][Aib8,Arg34]GLP-1-(7-36)amide; N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino}butyrylamino) butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyryl-amino)butyrylamino]ethoxy}ethoxy)acetyl][Aib8,Lys33,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoylsulfonyl)butyrylamino]dodecanoylamino}butyrylamino)butyrylamino]ethoxy}ethoxy)acetyl][Aib8,Arg34]GLP-1-(7-36)amide; N-epsilon26-[2-(2-{2-[2-(2-{2-[2-(2-{2-[2-(2-{2-[2-(2-{2-[2-(2-{2-[(S)-4-carboxy-4-((S)-4-carboxy-4-{12-[4-(16-(1H-tetrazol-5-yl)hexadecanoylsulfamoyl) butyrylamino]dodecanoylamino}butyrylamino)butyrylamino]ethoxy}ethoxy) acetylamino]ethoxy}ethoxy)acetylamino]ethoxy}ethoxy)acetylamino]ethoxy}ethoxy)acetylamino]ethoxy}ethoxy)acetyl][Aib8, Lys26,Arg34]GLP-1-(7-36)amide; N-epsilon37-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino}butyrylamino) butyrylamino]ethoxy}ethoxy)acetyl][Aib8,Glu22,Arg26,Arg34,Lys37]GLP-1-(7-37)amide; N-epsilon37-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino}butyrylamino) butyrylamino]ethoxy}ethoxy)acetyl][DesaminoHis7,Glu22,Arg26,Arg34,Lys37]GLP-1-(7-37)amide; N-epsilon37{2-[2-(2-{2-[2-((R)-3-carboxy-3-{[1-(19-carboxy-nonadecanoyl)piperidine-4-carbonyl]amino}propionylamino)ethoxy]ethoxy}acetylamino)ethoxy]ethoxy}acetyl [desaminoHis7,Glu22,Arg26,Arg34,Lys37]GLP-1(7-37)amide; N-epsilon37{2-[2-(2-{2-[2-((S)-3-carboxy-3-{[1-(19-carboxynonadecanoyl) piperidine-4-carbonyl]amino}propionylamino) ethoxy]ethoxy}acetylamino) ethoxy]ethoxy}acetyl [Aib8,Glu22, Arg26,Arg34, Lys37] GLP-1-(7-37)amide; N-epsilon37-[2-(2-[2-(2-[2-(2-((R)-3-[1-(17-carboxyhepta-decanoyl)piperidin-4-ylcarbonylamino]3-carboxy-propionylamino) ethoxy)ethoxy]acetylamino)ethoxy]ethoxy)acetyl][DesaminoHis7,Glu22,Arg26, Arg34,Phe(m-CF3)28] GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino)butyrylamino]ethoxy}ethoxy)acetylamino]ethoxy}ethoxy)acetyl][Aib8,Glu22,Arg26,Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexane-carbonyl}amino)butyrylamino]ethoxy}ethoxy) acetylamino]ethoxy}ethoxy)acetyl][DesaminoHis7,Glu22,Arg26,Arg34,Lys37]GLP-1-(7-37)amide; N-epsilon37-[2-(2-{2-[2-(2-{2-[(S)-4-carboxy-4-({trans-4-[(19-carboxy-nonadecanoylamino) methyl]cyclohexanecarbonyl}amino)butyrylamino]ethoxy}ethoxy)acetylamino]ethoxy}ethoxy)acetyl][DesaminoHis7,Glu22,Arg26,Glu30,Arg34, Lys37]GLP-1-(7-37); N-epsilon37-[2-(2-{2-[(S)-4-carboxy-4-((S)-4-carboxy-4-{12-[4-(16-(1H-tetrazol-5-yl)hexadecanoyl-sulfamoyl) butyrylamino]dodecanoylamino}butyrylamino) butyrylamino]ethoxy}ethoxy)acetyl][Aib8,Glu22,Arg26,Arg34,Lys37] GLP-1-(7-37)amide; N-epsilon37-[2-(2-{2-[(S)-4-carboxy-4-((S)-4-carboxy-4-{12-[4-(16-(1H-tetrazol-5-yl) hexadecanoylsulfamoyl) butyrylamino] dodecanoylamino}butyrylamino) butyrylamino] ethoxy}ethoxy)acetyl][DesaminoHis7,Glu22,Arg26,Arg34, Lys37]GLP-1-(7-37)amide; N-epsilon37-(3-((2-(2-(2-(2-(2-Hexadecyloxyethoxy)ethoxy)ethoxy) ethoxy) ethoxy))propionyl][DesaminoHis7,Glu22,Arg26,Arg34,Lys37] GLP-1(7-37)-amide; N-epsilon37-{2-(2-(2-(2-[2-(2-(4-(hexadecanoylamino)-4-carboxybutyryl-amino)ethoxy) ethoxy]acetyl)ethoxy)ethoxy)acetyl)}-[desaminoHis7, Glu22,Arg26, Glu30,Arg34,Lys37] GLP-1-(7-37)amide; N-epsilon37-{2-(2-(2-(2-[2-(2-(4-(hexadecanoylamino)-4-carboxy-butyryl-amino) ethoxy)ethoxy]acetyl)ethoxy) ethoxy) acetyl)}-[desaminoHis7,Glu22, Arg26, Arg34, Lys37]GLP-1-(7-37)amide; N-epsilon37-(2-(2-(2-(2-(2-(2-(2-(2-(octadecanoyl-amino)ethoxy)ethoxy) acetylamino) ethoxy) ethoxy)acetylamino)ethoxy)ethoxy) acetyl) [desaminoHis7,Glu22,Arg26,Arg34,Lys37] GLP-1 (7-37) amide; N-epsilon37-[4-(16-(1H-Tetrazol-5-yl) hexadecanoylsulfamoyl) butyryl][DesaminoHis7,Glu22, Arg26, Arg34, Lys37]GLP-1-(7-37)amide; N-epsilon37-[2-(2-{2-[2-(2-{2-[(S)-4-carboxy-4-(19-carboxynonadecanoylamino) butyrylamino]ethoxy}ethoxy) acetylamino]ethoxy}ethoxy)acetyl][DesaminoHis7,Glu22, Arg26, Arg34,Lys37]GLP-1-(7-37); N-epsilon37-(2-{2-[2-((S)-4-carboxy-4-{(S)-4-carboxy-4-[(S)-4-carboxy-4-(19-carboxy-nonadecanoylamino)butyrylamino] butyrylamino}butyrylamino)ethoxy]ethoxy}acetyl) [DesaminoHis7,Glu22,Arg26,Arg34,Lys37]GLP-1-(7-37); N-epsilon37-{2-[2-(2-{(S)-4-[(S)-4-(12-{4-[16-(2-tert-Butyl-2H-tetrazol-5-yl)-hexadecanoylsulfamoyl] butyrylamino}dodecanoylamino)-4-carboxybutyrylamino]-4-carboxybutyrylamino}ethoxy)ethoxy]acetyl} [DesaminoHis7,Glu22,Arg26,Arg34,Lys37] GLP-1 (7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl][Aib8,Glu22,Arg26,Arg34,Lys37]GLP-1-(7-37); N-alpha37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl][Aib8,Glu22,Arg26,Arg34,epsilon-Lys37]GLP-1-(7-37)peptide; N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl][desaminoHis7, Glu22,Arg26,Arg34,Lys37]GLP-1-(7-37); N-epsilon36-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl][desaminoHis7, Glu22,Arg26,Glu30,Arg34,Lys36] GLP-1-(7-37)-Glu-Lys peptide; N-epsilon37-[2-(2-{2-[2-(2-{2-[(S)-4-carboxy-4-({trans-4-[(19-carboxynonadecanoylamino)

methyl]cyclohexanecarbonyl}amino)butyryl-amino]
ethoxy}ethoxy)acetylamino]ethoxy}ethoxy)acetyl][Aib8,
Glu22,Arg26,Arg34,Lys37]GLP-1-(7-37); N-epsilon37-[2-
(2-{2-[2-(2-{2-[(S)-4-carboxy-4-(17-carboxy-
heptadecanoylamino)-butyrylamino]-ethoxy}-ethoxy)-
acetylamino]-ethoxy}-ethoxy)-acetyl]-[Aib8,Glu22, Arg26,
Arg34,Aib35,Lys37]GLP-1-(7-37); N-epsilon37-[(S)-4-
carboxy-4-(2-{2-[2-(2-{2-[2-(17-
carboxyheptadecanoylamino) ethoxy]ethoxy}acetylamino)
ethoxy]ethoxy}acetylamino) butyryl][Aib8,Glu22,Arg26,
34,Lys37] GLP-1 (7-37); N-epsilon37-[2-(2-[2-(2-[2-(2-[4-
(17-carboxyheptadecanoylamino)-4(S)-
carboxybutyrylamino]ethoxy)ethoxy]acetylamino)ethoxy]
ethoxy)acetyl][ImPr7,Glu22, Arg26,34,Lys37], GLP-1-(7-
37); N-epsilon26-{2-[2-(2-{2-[2-(2-{(S)-4-carboxy-4-[10-
(4-carboxyphenoxy) decanoylamino]butyrylamino}ethoxy)
ethoxy]acetylamino}ethoxy) ethoxy]acetyl}, N-epsilon37-
{2-[2-(2-{2-[2-(2-{(S)-4-carboxy-4-[10-(4-carboxy-
phenoxy)decanoylamino]butyrylamino}ethoxy)ethoxy]
acetylamino}ethoxy)ethoxy]acetyl}-[Aib8,Arg34,Lys37]
GLP-1(7-37)-OH; N-epsilon26 (17-carboxyhepta-
decanoyl)-[Aib8,Arg34]GLP-1-(7-37)-peptide;
N-epsilon26-(19-carboxynonadecanoyl)-[Aib8,Arg34]
GLP-1-(7-37); N-epsilon26-(4-{[N-(2-carboxyethyl)-N-
(15-carboxypenta-decanoyl)amino]methyl}benzoyl[Arg34]
GLP-1-(7-37); N-epsilon26-[2-(2-[2-(2-[2-(2-[4-(17-
carboxyheptadecanoylamino)-4(S)-carboxybutyrylamino]
ethoxy)ethoxy]acetylamino)ethoxy]ethoxy)acetyl][Aib8,
Arg34]GLP-1-(7-37); N-epsilon26-[2-(2-[2-(2-[2-(2-[4-(19-
carboxynonadecanoylamino)-4(S)-carboxybutyrylamino]
ethoxy)ethoxy]acetylamino)ethoxy]ethoxy)acetyl][Aib8,
Arg34]GLP-1-(7-37); N-epsilon26-[2-(2-[2-(2-[2-(2-[4-(17-
carboxyheptadecanoylamino)-4(S)-carboxybutyrylamino]
ethoxy)ethoxy]acetylamino)ethoxy]ethoxy)acetyl][3-(4-
Imidazolyl)Propionyl7,Arg34]GLP-1-(7-37); N-epsilon26-
[2-(2-[2-(2-[2-(2-[4-(17-carboxyheptadecanoylamino)-
(carboxymethyl-amino)acetylamino]ethoxy)ethoxy]
acetylamino)ethoxy]ethoxy)acetyl][Aib8,Arg34]GLP-1-(7-
37); N-epsilon26-[2-(2-[2-(2-[2-(2-[4-(17-
carboxyheptadecanoylamino)-3(S)-Sulfopropionylamino]
ethoxy)ethoxy]acetylamino)ethoxy]ethoxy)acetyl][Aib8,
Arg34]GLP-1-(7-37); N-epsilon26-[2-(2-[2-(2-[2-(2-[4-(17-
carboxyheptadecanoylamino)-4(S)-carboxybutyrylamino]
ethoxy)ethoxy]acetylamino)ethoxy]ethoxy)acetyl][Gly8,
Arg34] GLP-1-(7-37); N-epsilon26-[2-(2-[2-(2-[2-(2-[4-
(17-carboxyheptadecanoylamino)-4(S)-
carboxybutyrylamino]ethoxy)ethoxy]acetylamino)ethoxy]
ethoxy)acetyl][Aib8,Arg34]GLP-1-(7-37)-amide;
N-epsilon26-[2-(2-[2-(2-[2-(2-[4-(17-carboxyheptade-
canoylamino)-4(S)-carboxybutyrylamino]ethoxy)ethoxy]
acetylamino)ethoxy]ethoxy)acetyl][Aib8,Arg34,Pro37]
GLP-1-(7-37)amide; Aib8,Lys26(N-epsilon26-{2-(2-(2-(2-
[2-(2-(4-(pentadecanoylamino)-4-carboxybutyrylamino)
ethoxy)ethoxy]acetyl)ethoxy) ethoxy)acetyl)}), Arg34)
GLP-1H(7-37)-OH; N-epsilon26-[2-(2-[2-(2-[2-(2-[4-{[N-
(2-carboxyethyl)-N-(17-carboxyheptadecanoyl)amino]
methyl}benzoyl)amino]ethoxy) ethoxy]acetylamino)
ethoxy]ethoxy)acetyl][Aib8,Arg34]GLP-1(7-37);
N-alpha7-formyl, N-epsilon26-[2-(2-[2-(2-[2-(2-[4-(17-car-
boxyheptadecanoyl-amino)-4(S)-carboxybutyrylamino]
ethoxy)ethoxy]acetylamino)ethoxy]ethoxy)acetyl][Arg34]
GLP-1-(7-37); N-epsilon2626-[2-(2-[2-(2-[2-(2-[4-(17-
carboxyheptadecanoylamino)-4(S)-carboxybutyrylamino]
ethoxy)ethoxy]acetylamino)ethoxy]ethoxy)acetyl][Aib8,
Glu22, Arg34] GLP-1-(7-37); N-epsilon26{3-[2-(2-{2-[2-
(2-{2-[2-(2-[4-(15-(N—((S)-1,3-dicarboxypropyl) carbam-
oyl)pentadecanoylamino)-(S)-4-carboxybutyrylamino]
ethoxy)ethoxy]ethoxy}ethoxy)ethoxy]ethoxy}
ethoxy]propionyl} [Aib8,Arg34]GLP-1-(7-37);
N-epsilon26-[2-(2-[2-(2-[2-(2-[4-{[N-(2-carboxyethyl)-N-
(17-carboxy-heptadecanoyl)amino]methyl}benzoyl)amino]
(4(S)-carboxybutyryl-amino)ethoxy) ethoxy]acetylamino)
ethoxy]ethoxy)acetyl][Aib8,Arg34] GLP-1(7-37);
N-epsilon26-{(S)-4-carboxy-4-((S)-4-carboxy-4-((S)-4-car-
boxy-4-((S)-4-carboxy-4-(19-carboxy-nonadecanoylamino)
butyrylamino)butyrylamino)butyrylamino) butyrylamino}
[Aib8,Arg34]GLP-1-(7-37); N-epsilon26-4-(17-carboxy-
heptadecanoyl-amino)-4(S)-carboxybutyryl-[Aib8,Arg34]
GLP-1-(7-37); N-epsilon26-{3-[2-(2-{2-[2-(2-{2-[2-(2-[4-
(17-carboxyheptadecanoylamino)-4(S)-
carboxybutyrylamino]ethoxy)ethoxy]ethoxy}ethoxy)
ethoxy]ethoxy}ethoxy)ethoxy]propionyl}[Aib8,Arg34]
GLP-1-(7-37); N-epsilon26-{2-(2-(2-(2-[2-(2-(4-(17-
carboxyheptadecanoylamino)-4-carboxybutyrylamino)
ethoxy)ethoxy]acetyl)ethoxy)ethoxy)acetyl)}-[Aib-8,22,27,
30,35,Arg34,Pro37, Lys26] GLP-1 (7-37)amide; N-epsi-
lon26-[2-(2-[2-[4-(21-carboxyuneicosanoylamino)-4(S)-
carboxybutyrylamino]ethoxy]ethoxy)acetyl][Aib8,Arg34]
GLP-1-(7-37); and N-epsilon26-[2-(2-[2-(2-[2-(2-[4-(21-
carboxyuneicosanoylamino)-4(S)-carboxybutyrylamino]
ethoxy)ethoxy]acetylamino)ethoxy]ethoxy)acetyl][Aib8,
Arg34]GLP-1-(7-37).

In one embodiment GLP-1 peptides can be produced by appropriate derivatisation of an appropriate peptide backbone which has been produced by recombinant DNA technology or by peptide synthesis (e.g., Merrifield-type solid phase synthesis) as known in the art of peptide synthesis and peptide chemistry.

In one embodiment the production of peptides like GLP-1(7-37) and GLP-1 analogues is well known in the art. The GLP-1 moiety of the GLP-1 peptide of the invention (or fragments thereof) may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dorwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

In one embodiment GLP-1 peptides may be produced by recombinant methods, viz. by culturing a host cell containing a DNA sequence encoding the GLP-1 peptide and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

In one embodiment GLP-1 peptides of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Pharmaceutical Indications

The present invention also relates to a composition of the invention for use as a medicament.

In particular embodiments, the composition of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells; (iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atherosclerosis; mild chronic heart failure; angina pectoris; cardiac bypass reocclusion; intermittent claudication (atherosclerosisoblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

The following indications are particularly preferred: Type 2 diabetes, and/or obesity.

Particular Embodiments

1. A granule comprising a salt of N-(8-(2-hydroxybenzoyl) amino)caprylic acid and a lubricant, wherein the granule is obtained by mixing said salt of N-(8-(2-hydroxybenzoyl) amino)caprylic and said lubricant for more than 5 minutes, such as at least 10, 15, 20, 25, 30, 35, 40, 45 or 50 minutes.
2. A granule according to embodiment 1, wherein the duration of said mixing is at least 6 minutes, such as at least 7, 8, 9, 10, 11, 12, 13, 14, 15, 16, 17, 18, 19, 20, 21, 22, 23, 24, 25, 26, 27, 28, 29, 30, 35, 40, 45 or 50 minutes, such as at least 10, 20, 30, 40 or 50 minutes.
3. A granule according to any one of the preceding embodiments, wherein the amount of said lubricant is at least 0.25% (w/w) or at least 0.5% (w/w), such as at least 1% (w/w) or at least 2% (w/w), of said granule.
4. A granule according to any one of the preceding embodiments, wherein the amount of said lubricant is no more than 10% (w/w), such as no more than 8, 7, or 6% (w/w), of said granule.
5. A granule according to any one of the preceding embodiments, wherein said salt of N-(8-(2-hydroxybenzoyl)amino) caprylic acid is SNAC.
6. A granule according to any one of the preceding embodiments, wherein said lubricant is magnesium stearate.
7. A granule according to any one of the preceding embodiments, wherein said granule comprises granules which have been manufactured by dry granulation, such as roller compaction.
8. A granule according to any one of the preceding embodiments, wherein the duration of said mixing is at least 10, 20, 30, 40 or 50 minutes, such as at least 30 minutes or at least 40 minutes, such as at least 50 minutes.
9. A granule according to any one of the preceding embodiments, wherein the duration of said mixing is no more than 12 hours, such as no more than 10, 8, 6, 4, or 2 hours.
10. A composition comprising said granule as defined in any one of the preceding embodiments,
11. A pharmaceutical composition according to any one of the preceding embodiments, wherein said composition further comprises a pharmaceutically active ingredient.
12. A pharmaceutical composition according to any one of the preceding embodiments, wherein said composition further comprises a GLP-1 peptide.
13. A pharmaceutical composition according to embodiment 4, wherein said GLP-1 peptide comprises an albumin binding moiety.
14. A pharmaceutical composition according to embodiment 4, wherein said GLP-1 peptide is N-epsilon26-[2-(2-{2-[2-(2-{2-[(S)-4-carboxy-4-(17-carboxyheptadecanoylamino) butyrylamino]ethoxy}ethoxy)acetylamino]ethoxy}ethoxy) acetyl][Aib8,Arg34]GLP-1(7-37).
15. A composition according to any one of the preceding embodiments, wherein said composition further comprises one or more pharmaceutically acceptable excipients.
16. A composition according to any one of the preceding embodiments, wherein said composition further comprises one or more ingredients selected from the group consisting of a filler, such as microcrystalline cellulose, and a binder, such as povidone.
17. A composition according to any one of the preceding embodiments, wherein said further comprises extragranular lubricant, such as magnesium stearate.

18. A composition according to any one of the preceding embodiments, wherein said composition comprises granules which have been manufactured by dry granulation.

19. A composition according to embodiment 13, wherein said composition comprises granules which have been manufactured by roller compaction.

20. A composition according to any one of the preceding embodiments, wherein said composition is in the form of a solid dosage form.

21. A composition according to embodiment 20, wherein said solid dosage form is a tablet.

22. A composition according to embodiment 20, wherein said composition is in the form of a capsule.

23. A composition according to embodiment 20, wherein said composition is in the form of a sachet.

24. A process of producing a pharmaceutical composition comprising granules comprising a salt of N-(8-(2-hydroxybenzoyl)amino)caprylic acid and a lubricant, such a magnesium stearate, wherein said process comprises the steps:
a) mixing said salt of N-(8-(2-hydroxybenzoyl)amino)caprylic acid and said lubricant for more than 5 minutes; and
b) optionally roller compacting the mixture of step a.

25. A process according to embodiment 24, wherein the duration of said mixing in step a is at least 6 minutes, such as at least 7, 8, 9, 10, 11, 12, 13, 14, 15, 16, 17, 18, 19, 20, 21, 22, 23, 24, 25, 26, 27, 28, 29, 30, 35, 40, 45 or 50 minutes. 26. A process according to embodiment 24 or 25, wherein the duration of said mixing in step a is at least 20 minutes, such as at least 30 minutes, at least 40 minutes or at least 50 minutes.

27. A process according to any one of embodiments 24-26, wherein the amount of said lubricant is at least 0.25% (w/w) or at least 0.5% (w/w), such as at least 1% (w/w) or at least 2% (w/w), of said composition.

28. A process according to any one of embodiments 24-27, wherein the duration of said mixing in step a is at least at least 10, 20, 30, 40 or 50 minutes, such as 30 minutes or at least 40 minutes, such as at least 50 minutes.

29. A process according to any one of embodiments 24-28, wherein the amount of said lubricant is at least 1% (w/w), such as at least 2% (w/w), of said composition.

30. A process according to any one of embodiments 24-29, wherein, wherein the amount of said lubricant is no more than 10% (w/w), such as no more than 8, 7, or 6% (w/w), of said composition.

31. A process according to any one of embodiments 24-30, wherein said lubricant is magnesium stearate.

32. A process according to any one of embodiments 24-31, wherein said salt of N-(8-(2-hydroxybenzoyl)amino) caprylic acid is SNAC.

33. A process according to any one of embodiments 24-32, wherein said composition further comprises one or more pharmaceutically acceptable excipients.

34. A process according to any one of embodiments 24-33, wherein said composition further comprises a filler, such as microcrystalline cellulose.

35. A process according to any one of embodiments 24-34, wherein said composition further comprises a binder, such as povidone.

36. A process according to any one of embodiments 24-35, wherein said composition is in the form of a solid dosage form.

37. A process composition according to embodiment 36, wherein said composition is a tablet.

38. A process composition according to embodiment 36, wherein said composition is in the form of a capsule.

39. A process composition according to embodiment 36, wherein said composition is in the form of a sachet.

40. A process according to any one of embodiments 24-39, wherein the duration of said mixing in step a is no more than 12 hours, such as no more than 10, 8, 6, 4, or 2 hours.

41. A granule obtained by the process as defined in any one of embodiments 24-40.

42. A pharmaceutical composition obtained by the process as defined in any one of embodiments 24-40.

43. A granule as defined in any one of embodiments 1-9 or 41 or a composition as defined in any one of embodiments 10-23 or 42 for use in medicine.

44. A granule as defined in any one of embodiments 1-9 or 41 or a composition as defined in any one of embodiments 10-23 or 42 for treatment of diabetes or obesity.

45. A granule or a composition according to embodiment 43 or 44, wherein said composition or said granule is administered orally.

46. A method for treatment of diabetes or obesity comprising administering a granule as defined in any one of embodiments 1-9 or 41 or a composition as defined in any one of embodiments 10-23 or 42 to a patient in need thereof.

47. A method according to embodiment 46, wherein said composition or said granule is administered orally.

48. A granule as defined in any one of embodiments 1-9 or 41 or a composition as defined in any one of embodiments 10-23 or 42 for use in medicine, such as for treatment of diabetes or obesity, wherein said composition or said granule is optionally administered orally.

Further Particular Embodiments

The following are further particular embodiments of the invention:

1. A pharmaceutical composition comprising a salt of N-(8-(2-hydroxybenzoyl)amino)caprylic acid and a lubricant, wherein the composition is obtained by mixing said salt of N-(8-(2-hydroxybenzoyl)amino)caprylic and said lubricant for more than 5 minutes.

2. A composition according to embodiment 1, wherein the duration of said mixing is at least 6 minutes, such as at least 7, 8, 9, 10, 11, 12, 13, 14, 15, 16, 17, 18, 19, 20, 21, 22, 23, 24, 25, 26, 27, 28, 29, 30, 35, 40, 45 or 50 minutes, such as at least 10, 20, 30, 40 or 50 minutes.

3. A composition according to embodiment 1 or 2, wherein the amount of said lubricant is at least 0.25% (w/w) or at least 0.5% (w/w), such as at least 1% (w/w) or at least 2% (w/w), of said composition.

4. A composition according to any one of the preceding embodiments, wherein the amount of said lubricant is no more than 10% (w/w), such as no more than 8, 7, or 6% (w/w), of said composition.

5. A composition according to any one of the preceding embodiments, wherein said salt of N-(8-(2-hydroxybenzoyl) amino)caprylic acid is SNAC.

6. A composition according to any one of the preceding embodiments, wherein said composition further comprises a pharmaceutically active ingredient.

7. A composition according to any one of the preceding embodiments, wherein said composition further comprises a GLP-1 peptide.

8. A according to embodiment 7, wherein said GLP-1 peptide comprises an albumin binding moiety.

9. A composition according to embodiment 7 or 8, wherein said GLP-1 peptide is N-epsilon26-[2-(2-{2-[2-(2-{2-[(S)-

4-carboxy-4-(17-carboxyheptadecanoylamino) butyry-lamino]ethoxy}ethoxy)acetylamino]ethoxy}ethoxy)acetyl][Aib8,Arg34]GLP-1(7-37).

10. A composition according to any one of the preceding embodiments, wherein said lubricant is magnesium stearate.

11. A composition according to any one of the preceding embodiments, wherein said composition further comprises one or more ingredients selected from the group consisting of a filler, such as microcrystalline cellulose, and a binder, such as povidone.

12. A composition according to any one of the preceding embodiments, wherein said composition further comprises one or more pharmaceutically acceptable excipients.

13. A composition according to any one of the preceding embodiments, wherein said composition comprises granules which have been manufactured by dry granulation.

14. A composition according to embodiment 13, wherein said composition comprises granules which have been manufactured by roller compaction.

15. A composition according to any one of the preceding embodiments, wherein said composition is in the form of a solid dosage form.

16. A composition according to embodiment 15, wherein said solid dosage form is a tablet.

17. A composition according to embodiment 15, wherein said composition is in the form of a capsule.

18. A composition according to embodiment 15, wherein said composition is in the form of a sachet.

19. A composition according to any one of embodiments 1-18, wherein the duration of said mixing is at least 10, 20, 30, 40 or 50 minutes, such as at least 30 minutes or at least 40 minutes, such as at least 50 minutes.

20. A composition according to any one of embodiments 1-19, wherein the duration of said mixing is no more than 12 hours, such as no more than 10, 8, 6, 4, or 2 hours.

21. A process of producing a pharmaceutical composition comprising a salt of N-(8-(2-hydroxybenzoyl)amino) caprylic acid and a lubricant, such a magnesium stearate, wherein said process comprises the steps:
  a. mixing said salt of N-(8-(2-hydroxybenzoyl)amino) caprylic acid and said lubricant for more than 5 minutes; and
  b. optionally roller compacting the mixture of step a.

22. A process according to embodiment 21, wherein the duration of said mixing in step a is at least 6 minutes, such as at least 7, 8, 9, 10, 11, 12, 13, 14, 15, 16, 17, 18, 19, 20, 21, 22, 23, 24, 25, 26, 27, 28, 29, 30, 35, 40, 45 or 50 minutes.

23. A process according to embodiment 21 or 22, wherein the duration of said mixing in step a is at least at least 10, 20, 30, 40 or 50 minutes, such as 30 minutes or at least 40 minutes, such as at least 50 minutes.

24. A process according to any one of embodiments 21-23, wherein the amount of said lubricant is at least 1% (w/w), such as at least 2% (w/w), of said composition.

25. A process according to any one of embodiments 21-24, wherein, wherein the amount of said lubricant is no more than 10% (w/w), such as no more than 8, 7, or 6% (w/w), of said composition.

26. A process according to any one of embodiments 21-25, wherein said lubricant is magnesium stearate.

27. A process according to any one of embodiments 21-26, wherein said salt of N-(8-(2-hydroxybenzoyl)amino) caprylic acid is SNAC.

28. A process according to any one of embodiments 21-27, wherein said composition further comprises one or more pharmaceutically acceptable excipients.

29. A process according to any one of embodiments 21-28, wherein said composition further comprises a filler, such as microcrystalline cellulose.

30. A process according to any one of embodiments 21-29, wherein said composition further comprises a binder, such as povidone.

31. A process according to any one of embodiments 21-30, wherein said composition is in the form of a solid dosage form.

32. A process composition according to embodiment 31, wherein said composition is a tablet.

33. A process composition according to embodiment 31, wherein said composition is in the form of a capsule.

34. A process composition according to embodiment 31, wherein said composition is in the form of a sachet.

35. A process according to any one of embodiments 21-34, wherein the duration of said mixing in step a is no more than 12 hours, such as no more than 10, 8, 6, 4, or 2 hours.

36. A composition obtained by the process as defined in any one of embodiments 21-35.

37. A granule obtained by the process as defined in any one of embodiments 21-35.

38. A composition as defined in any one of embodiments 1-20 or 36 or a granule as defined in embodiment 37 for use in medicine.

39. A composition as defined in any one of embodiments 1-20 or 36 or a granule as defined in embodiment 37 for treatment of diabetes or obesity.

40. A composition according to embodiment 38 or 39, wherein said composition or said granule is administered orally.

41. A method for treatment of diabetes or obesity comprising administering the composition as defined in any one of embodiments 1-20 or 36 or a granule as defined in embodiment 37 to a patient in need thereof.

42. A method according to embodiment 41, wherein said composition or said granule is administered orally.

EXAMPLES

Materials and Methods

General Methods of Preparation

Dry Granulation

Dry granulation was carried out by roller compaction on a GerteisMINI-PACTOR using smooth rolls, a 0.63 mm wire mesh screen, and a granulator speed of 60 rpm. The roll speed was set at 1.5 or 3.0 rpm and roller compaction forces around 1 to 13 kN/cm were applied at a gap of 1.0 mm. Subsequent to dry granulation commination of the moldings into granules was carried out.

Tablet Preparation

Tablets were produced on a Korsch PH106 or a Fette 102i mounted with a gravity feeder and one or four punches, respectively, resulting in 13 mm×7.5 mm convex oval tablets having no score. For the Korsch PH106 the press speed was set around 25 rpm and the counter pressure was adjusted to 40 kN. For the Fette 102i the press speed was set at 20 rpm. The fill volume was adjusted to obtain tablets having target weights from 404 to 414 mg and compression forces around 2 to 17 kN were applied.

General Methods of Detection and Characterisation

Resistance to Crushing of Tablets

Resistance to crushing of tablets was determined according to section 2.9.8 in the European Pharmacopoeia 7.5, 7th edition 2012 and at a jaw speed of 20 N/s.

Friability

Friability was determined according to section 2.9.7 in the European Pharmacopoeia 7.5, 7th edition 2012.

Particle Size

Particle size, i.e. the volume distribution of equivalent spherical diameters, was determined by laser diffraction at 3 bar dispersive pressure and at a obscuration in the range from 0.05-8% in a Malvern Mastersizer 2000 Scirocco 2000 (dry mode) using general purpose enhanced sensitivity (Mie approximation) and a refractive index of 1.65.

Disintegration Time

Disintegration time was determined according to section 2.9.1 in the European Pharmacopoeia 7.5, 7th edition 2012 and the liquid medium used for the disintegration test was water-R as defined in the European Pharmacopoeia 7.5, 7th edition 2012.

Compression Force

Compression force, i.e. the force exerted between the upper and lower punch when compressing materials into a tablet, was determined by a load cell transducer that converted the force into electrical signal using a strain gauge.

Roller Compaction Force

Roller compaction force, i.e. the force exerted between the rolls of the roller compactor when compacting materials into a continuous strip of compressed material, was determined by a pressure transducer that converts the hydraulic pressure into electrical signal; the roller compaction force may be measured in kiloNewton (kN) or in kiloNewton per roll width (kN/cm).

Example 1

Preparation and Characterisation of Compositions Comprising Different Amounts of Lubricant Three granule compositions each containing 2, 2.5, or 5% (w/w) of magnesium stearate, respectively, were manufactured for three different tablet compositions; their compositions are described in Table 1.

TABLE 1

Composition of tablets

| Component | Granule Fraction/ Extragranular | Composition type | | |
|---|---|---|---|---|
| | | A | B | C |
| SNAC | First granule fraction | 300 mg/tablet | 300 mg/tablet | 300 mg/tablet |
| Magnesium stearate | First granule fraction | 2% (w/w) 6 mg/tablet | 2.5% (w/w) 8 mg/tablet | 5% (w/w) 16 mg/tablet |
| Microcrystalline cellulose (Avicel PH 101) | Second granule fraction | 90 mg/tablet | 90 mg/tablet | 90 mg/tablet |
| Povidone K 90 (Kollidon 90F) | Extragranular | 8 mg/tablet | 8 mg/tablet | 8 mg/tablet |
| Tablet weight | | 404 mg | 406 mg | 414 mg |

The tablet compositions were prepared by mixing the delivery agent SNAC and magnesium stearate at 25 rpm prior to dry granulation; the mixing time of enhancer and lubricant prior to granulation for each experiment is shown in Table 2.

TABLE 2

Preparation of tablets

| | Exp. 1 | Exp. 2 | Exp. 3 | Exp. 4 | Exp. 5 |
|---|---|---|---|---|---|
| Composition type | A | C | A | C | B |
| Amount of magnesium stearate (% (w/w)) | 2.0 | 5.0 | 2.0 | 5.0 | 2.5 |
| Mixing time of first granule fraction (i.e. delivery agent and lubricant) (min) | 40 | 40 | 4 | 4 | 20 |

Dry granulation was carried out as described in the section General Methods of Preparation. Particles <180 μm were removed from both granule fractions prior to weighing and blending for the tabletting process. The blending prior to the tabletting process was performed for 5 min at 32 rpm. Tabletting was carried out as described in the section General Methods of Preparation.

The particle size of the first granule fraction in the tablet compositions were characterised by laser diffraction as described in the section General Methods of Detection and Characterisation. The results are shown in Table 3.

TABLE 3

Particle sizes of granules determined by laser diffraction.

| | Volume % (v/v) | | | | |
|---|---|---|---|---|---|
| Size (μm) | Exp. 1 | Exp. 2 | Exp. 3 | Exp. 4 | Exp. 5 |
| 0.011 | 0.00 | 0.00 | 0.00 | 0.00 | 0.00 |
| 0.013 | 0.00 | 0.00 | 0.00 | 0.00 | 0.00 |
| 0.015 | 0.00 | 0.00 | 0.00 | 0.00 | 0.00 |
| 0.017 | 0.00 | 0.00 | 0.00 | 0.00 | 0.00 |
| 0.020 | 0.00 | 0.00 | 0.00 | 0.00 | 0.00 |
| 0.023 | 0.00 | 0.00 | 0.00 | 0.00 | 0.00 |
| 0.026 | 0.00 | 0.00 | 0.00 | 0.00 | 0.00 |
| 0.030 | 0.00 | 0.00 | 0.00 | 0.00 | 0.00 |
| 0.035 | 0.00 | 0.00 | 0.00 | 0.00 | 0.00 |
| 0.040 | 0.00 | 0.00 | 0.00 | 0.00 | 0.00 |
| 0.046 | 0.00 | 0.00 | 0.00 | 0.00 | 0.00 |
| 0.052 | 0.00 | 0.00 | 0.00 | 0.00 | 0.00 |
| 0.060 | 0.00 | 0.00 | 0.00 | 0.00 | 0.00 |
| 0.069 | 0.00 | 0.00 | 0.00 | 0.00 | 0.00 |
| 0.079 | 0.00 | 0.00 | 0.00 | 0.00 | 0.00 |

TABLE 3-continued

Particle sizes of granules determined by laser diffraction.

| Size (μm) | Exp. 1 | Exp. 2 | Exp. 3 | Exp. 4 | Exp. 5 |
|---|---|---|---|---|---|
| 0.091 | 0.00 | 0.00 | 0.00 | 0.00 | 0.00 |
| 0.105 | 0.00 | 0.00 | 0.00 | 0.00 | 0.00 |
| 0.120 | 0.00 | 0.00 | 0.00 | 0.00 | 0.00 |
| 0.138 | 0.00 | 0.00 | 0.00 | 0.00 | 0.00 |
| 0.158 | 0.00 | 0.00 | 0.00 | 0.00 | 0.00 |
| 0.182 | 0.00 | 0.00 | 0.00 | 0.00 | 0.00 |
| 0.209 | 0.00 | 0.00 | 0.00 | 0.00 | 0.00 |
| 0.240 | 0.00 | 0.00 | 0.00 | 0.00 | 0.00 |
| 0.275 | 0.00 | 0.00 | 0.00 | 0.00 | 0.00 |
| 0.316 | 0.00 | 0.00 | 0.00 | 0.00 | 0.00 |
| 0.363 | 0.00 | 0.00 | 0.00 | 0.00 | 0.00 |
| 0.417 | 0.00 | 0.00 | 0.00 | 0.00 | 0.00 |
| 0.479 | 0.00 | 0.00 | 0.00 | 0.00 | 0.00 |
| 0.550 | 0.00 | 0.00 | 0.00 | 0.00 | 0.00 |
| 0.631 | 0.00 | 0.00 | 0.02 | 0.00 | 0.00 |
| 0.724 | 0.05 | 0.05 | 0.10 | 0.05 | 0.04 |
| 0.832 | 0.13 | 0.12 | 0.17 | 0.12 | 0.10 |
| 0.955 | 0.23 | 0.22 | 0.29 | 0.22 | 0.19 |
| 1.096 | 0.35 | 0.32 | 0.41 | 0.32 | 0.28 |
| 1.259 | 0.49 | 0.45 | 0.56 | 0.45 | 0.40 |
| 1.445 | 0.66 | 0.59 | 0.75 | 0.60 | 0.54 |
| 1.660 | 0.86 | 0.74 | 0.97 | 0.76 | 0.70 |
| 1.905 | 1.10 | 0.91 | 1.23 | 0.94 | 0.87 |
| 2.188 | 1.35 | 1.09 | 1.52 | 1.13 | 1.05 |
| 2.512 | 1.62 | 1.27 | 1.83 | 1.32 | 1.23 |
| 2.884 | 1.90 | 1.44 | 2.16 | 1.50 | 1.40 |
| 3.311 | 2.16 | 1.59 | 2.47 | 1.67 | 1.55 |
| 3.802 | 2.40 | 1.71 | 2.74 | 1.80 | 1.68 |
| 4.365 | 2.58 | 1.79 | 2.96 | 1.90 | 1.77 |
| 5.012 | 2.70 | 1.84 | 3.10 | 1.95 | 1.81 |
| 5.754 | 2.73 | 1.83 | 3.13 | 1.95 | 1.80 |
| 6.607 | 2.68 | 1.77 | 3.05 | 1.89 | 1.74 |
| 7.586 | 2.53 | 1.66 | 2.87 | 1.77 | 1.63 |
| 8.710 | 2.30 | 1.51 | 2.59 | 1.62 | 1.47 |
| 10.000 | 2.00 | 1.34 | 2.24 | 1.43 | 1.29 |
| 11.482 | 1.67 | 1.16 | 1.85 | 1.23 | 1.09 |
| 13.183 | 1.34 | 0.98 | 1.46 | 1.03 | 0.90 |
| 15.136 | 1.03 | 0.82 | 1.10 | 0.86 | 0.73 |
| 17.378 | 0.78 | 0.70 | 0.80 | 0.72 | 0.59 |
| 19.953 | 0.59 | 0.63 | 0.58 | 0.62 | 0.51 |
| 22.909 | 0.48 | 0.60 | 0.44 | 0.57 | 0.47 |
| 26.303 | 0.44 | 0.62 | 0.38 | 0.57 | 0.48 |
| 30.200 | 0.46 | 0.67 | 0.38 | 0.60 | 0.52 |
| 34.674 | 0.52 | 0.74 | 0.41 | 0.67 | 0.59 |
| 39.811 | 0.60 | 0.82 | 0.47 | 0.75 | 0.68 |
| 45.709 | 0.70 | 0.92 | 0.55 | 0.85 | 0.78 |
| 52.481 | 0.80 | 1.03 | 0.65 | 0.97 | 0.89 |
| 60.256 | 0.92 | 1.15 | 0.75 | 1.10 | 1.03 |
| 69.183 | 1.06 | 1.30 | 0.88 | 1.26 | 1.18 |
| 79.433 | 1.22 | 1.48 | 1.03 | 1.44 | 1.36 |
| 91.201 | 1.40 | 1.69 | 1.21 | 1.64 | 1.56 |
| 104.713 | 1.61 | 1.93 | 1.41 | 1.87 | 1.80 |
| 120.226 | 1.86 | 2.20 | 1.64 | 2.12 | 2.07 |
| 138.038 | 2.13 | 2.51 | 1.89 | 2.40 | 2.37 |
| 158.489 | 2.45 | 2.86 | 2.17 | 2.71 | 2.73 |
| 181.970 | 2.80 | 3.25 | 2.46 | 3.05 | 3.14 |
| 208.930 | 3.19 | 3.69 | 2.79 | 3.44 | 3.62 |
| 239.883 | 3.59 | 4.16 | 3.12 | 3.86 | 4.15 |
| 275.423 | 4.01 | 4.65 | 3.46 | 4.32 | 4.71 |
| 316.228 | 4.39 | 5.10 | 3.79 | 4.75 | 5.24 |
| 363.078 | 4.69 | 5.45 | 4.06 | 5.12 | 5.67 |
| 416.869 | 4.85 | 5.62 | 4.24 | 5.34 | 5.91 |
| 478.630 | 4.81 | 5.52 | 4.28 | 5.34 | 5.87 |
| 549.541 | 4.51 | 5.10 | 4.13 | 5.05 | 5.48 |
| 630.957 | 3.94 | 4.34 | 3.77 | 4.46 | 4.74 |
| 724.436 | 3.10 | 3.27 | 3.20 | 3.59 | 3.70 |
| 831.764 | 2.14 | 2.07 | 2.49 | 2.53 | 2.50 |
| 954.993 | 0.98 | 0.73 | 1.71 | 1.40 | 1.24 |
| 1096.478 | 0.12 | 0.00 | 0.94 | 0.38 | 0.17 |
| 1258.925 | 0.00 | 0.00 | 0.26 | 0.00 | 0.00 |
| 1445.440 | 0.00 | 0.00 | 0.05 | 0.00 | 0.00 |
| 1659.570 | 0.00 | 0.00 | 0.00 | 0.00 | 0.00 |
| 1905.461 | 0.00 | 0.00 | 0.00 | 0.00 | 0.00 |
| 2187.762 | 0.00 | 0.00 | 0.00 | 0.00 | 0.00 |
| 2511.886 | 0.00 | 0.00 | 0.00 | 0.00 | 0.00 |
| 2884.032 | 0.00 | 0.00 | 0.00 | 0.00 | 0.00 |
| 3311.311 | 0.00 | 0.00 | 0.00 | 0.00 | 0.00 |
| 3801.894 | 0.00 | 0.00 | 0.00 | 0.00 | 0.00 |
| 4365.158 | 0.00 | 0.00 | 0.00 | 0.00 | 0.00 |
| 5011.872 | 0.00 | 0.00 | 0.00 | 0.00 | 0.00 |
| 5754.399 | 0.00 | 0.00 | 0.00 | 0.00 | 0.00 |
| 6606.934 | 0.00 | 0.00 | 0.00 | 0.00 | 0.00 |
| 7585.776 | 0.00 | 0.00 | 0.00 | 0.00 | 0.00 |
| 8709.636 | 0.00 | 0.00 | 0.00 | 0.00 | 0.00 |
| 10000.000 | 0.00 | 0.00 | 0.00 | 0.00 | 0.00 |

Resistance to crushing and compression force of the tablets were determined as described in the section General Methods of Detection and Characterisation. The results are shown in Table 4.

TABLE 4

Tablet resistance to crushing as a function of the compression force for the experiments.

| Exp. 1 | | Exp. 2 | | Exp. 3 | | Exp. 4 | | Exp. 5 | |
|---|---|---|---|---|---|---|---|---|---|
| CF[1] (kN) | TRC[2] (N) | CF (kN) | TRC (N) | CF (kN) | TRC (N) | CF (kN) | TRC (N) | CF (kN) | TRC (N) |
| 3.4 | 48.6 | 2.3 | 25.4 | 3.4 | 53.1 | 2.3 | 24.5 | 2.6 | 31.1 |
| 4.8 | 85.4 | 3.6 | 47.2 | 5.5 | 94.6 | 3.5 | 43.3 | 3.6 | 49.8 |
| 8.2 | 139.0 | 5.9 | 81.8 | 8.5 | 142.7 | 5.9 | 78.5 | 5.7 | 87.2 |
| 11.3 | 180.6 | 9.2 | 122.6 | 9.6 | 164.1 | 9.6 | 123.6 | 7.7 | 116.9 |
| 14.8 | 208.8 | 14.3 | 153.6 | 12.4 | 185.6 | 13.9 | 148.3 | 10.5 | 160.2 |
| 17.1 | 226.8 | 16.6 | 168.3 | 15.1 | 210.6 | 16.6 | 161.2 | 12.6 | 180.9 |
| — | — | — | — | — | — | — | — | 15.3 | 189.4 |
| — | — | — | — | — | — | — | — | 17.0 | 195.3 |

[1]CF: Compression force.
[2]TRC: Tablet resistance to crushing.

Disintegration time and compression force of the tablets were determined as described in the section General Methods of Detection and Characterisation. The results are shown in Table 5.

TABLE 5

Tablet disintegration time as a function of the compression force for the experiments.

| Exp. 1 | | Exp. 2 | | Exp. 3 | | Exp. 4 | | Exp. 5 | |
|---|---|---|---|---|---|---|---|---|---|
| CF[1] (kN) | TDT[2] (min) | CF (kN) | TDT (min) | CF (kN) | TDT (min) | CF (kN) | TDT (min) | CF (kN) | TDT (min) |
| 3.4 | 4.8 | 2.3 | 5.1 | 3.4 | 5.7 | 2.3 | 3.9 | 2.6 | 3.5 |
| 4.8 | 6.7 | 3.6 | 7.4 | 5.5 | 7.2 | 3.5 | 5.9 | 3.6 | 5.1 |
| 8.2 | 8.1 | 5.9 | 9.4 | 8.5 | 8.1 | 5.9 | 7.9 | 5.7 | 6.6 |
| 11.3 | 7.8 | 9.2 | 9.2 | 9.6 | 7.4 | 9.6 | 8.7 | 7.7 | 7.4 |
| 14.8 | 8.1 | 14.3 | 10.2 | 12.4 | 8.8 | 13.9 | 10.2 | 10.5 | 8.6 |
| 17.1 | 8.7 | 16.6 | 10.8 | 15.1 | 8.0 | 16.6 | 11.4 | 12.6 | 8.7 |
| — | — | — | — | — | — | — | — | 15.3 | 8.8 |
| — | — | — | — | — | — | — | — | 17.0 | 8.0 |

[1]CF: Compression force.
[2]TDT: Tablet disintegration time.

Friability of the tablets was determined as described in the section General Methods of Detection and Characterisation. The friability of the tablets from experiment 1-5 was found to be <0.2% (w/w).

These results show that for each of the three compositions A, B and C, the time used to mix the blend of magnesium stearate and SNAC (4, 20, or 40 minutes) prior to granulation did not influence the size of the granules (see Table 3) whereas the extent of granulation was increased with increasing mixing time. In addition, the crushing strength (see Table 4), the disintegration time (see Table 5) and the friability (<0.2% (w/w)) of the tablets from experiment 1-5 were not influenced by the mixing time used to mix magnesium stearate and SNAC prior to granulation.

Example 2

Preparation and Characterisation of Compositions Prepared Using Different Granulation Methods Tablet compositions containing the components shown in Table 6 were prepared using different methods of preparation.

TABLE 6

Composition of tablets

| Components | Granule Fraction/ Extragranular | Composition Type D | Composition Type E |
|---|---|---|---|
| SNAC | First granule fraction | 300 mg/tablet | 300 mg/tablet |
| Magnesium stearate | | 7.7 mg/tablet | 7.7 mg/tablet |
| Microcrystalline cellulose (Avicel PH 101) | | None | 57 mg/tablet |
| Microcrystalline cellulose (Avicel PH 101) | Second granule fraction | 90 mg/tablet | 33 mg/tablet |
| Povidone K 90 (Kollidon 90F) | | 8 mg/tablet | 8 mg/tablet |
| Magnesium stearate | Extragranular | 2 mg/tablet | 2 mg/tablet |
| Tablet weight | | 407.7 mg | 407.7 mg |

Tablets with Composition Type E were made by preparing two granule fractions by dry granulation; the first granule fraction contained the delivery agent SNAC, microcrystalline cellulose and 2.1% magnesium stearate and the second granule fraction contained microcrystalline cellulose and povidone. A two-step mixing procedure was performed for the first granule fraction, i.e. containing SNAC, prior to the dry granulation process: In the first mixing step SNAC and magnesium stearate was mixed for 50 minutes at 25 rpm and in the second mixing step microcrystalline cellulose was added to the SNAC/magnesium stearate blend and mixed for another 5, 20, or 25 min at 25 rpm; thus, the lubrication process was performed for a total of 55, 70, or 75 minutes, respectively, at 25 rpm prior to dry granulation. For the second granule fraction, i.e. containing microcrystalline cellulose and povidone the mixing was performed for 40 min at 25 rpm, prior to dry granulation. Dry granulation was carried out as described in the section General Methods of Preparation. Particles <90 μm were removed from the first granule fraction prior to weighing and blending with the second granule fraction and extragranular magnesium stearate. The two granule fractions were mixed for 10 min at 25 rpm before extragranular magnesium stearate was mixed with the two granule fractions for additional 2 minutes at 25 rpm prior to the tabletting process. Tablets were prepared as described in the section General Methods of Preparation.

Tablets with Composition Type D were made by preparing two granule fractions by dry granulation; the first granule fraction contained the delivery agent SNAC and 2.5% magnesium stearate and the second granule fraction contained microcrystalline cellulose and povidone. SNAC and magnesium stearate were mixed for 20, 50, or 75 min, respectively, at 25 rpm prior to dry granulation. For the second granule fraction, i.e. containing microcrystalline cellulose and povidone, the mixing was performed for 20 min at 25 rpm, prior to dry granulation. Dry granulation was carried out as described in the section General Methods of Preparation. Particles <90 μm were removed from the first granule fraction prior to weighing and blending with the second granule fraction and extragranular magnesium stearate. The two granule fractions were mixed for 10 min at 25 rpm before extra granular magnesium stearate was mixed with the two granule fractions for additional 2 minutes at 25 rpm prior to the tabletting process. Tablets were prepared as described in the section General Methods of Preparation.

The mixing time prior to granulation of the first granule fraction for each experiment is shown in Table 7.

TABLE 7

Preparation of the first granule fraction

| | Exp. V | Exp. VI | Exp. VII | Exp. VIII | Exp. IX | Exp. X |
|---|---|---|---|---|---|---|
| Composition type | D | D | D | E | E | E |
| First mixing time[1] (min) | 75 | 20 | 50 | 50 | 50 | 50 |
| Second mixing time[2] (min) | | | | 25 | 5 | 20 |
| Total mixing time of intragranular lubricant (min) | 75 | 20 | 50 | 75 | 55 | 70 |

[1]The first mixing time is the mixing time of enhancer and lubricant only.
[2]The second mixing time is the mixing time of enhancer/lubricant blend and microcrystalline cellulose.

The first granule fractions were characterised by laser diffraction as described in the section General Methods of Detection and Characterisation. The results are shown in Tables 8-13 as a function of the roller compaction force used to prepare the first granule fraction.

TABLE 8

Particle sizes of the first granule fraction for experiment V (mixing time of 75 min prior to granulation) determined by laser diffraction and shown as a function of the roller compaction force.

| | Volume in % (v/v) Exp. V | | | |
|---|---|---|---|---|
| Size (μm) | 4 kN/cm | 7 kN/cm | 10 kN/cm | 13 kN/cm |
| 0.011 | 0.00 | 0.00 | 0.00 | 0.00 |
| 0.013 | 0.00 | 0.00 | 0.00 | 0.00 |
| 0.015 | 0.00 | 0.00 | 0.00 | 0.00 |
| 0.017 | 0.00 | 0.00 | 0.00 | 0.00 |
| 0.020 | 0.00 | 0.00 | 0.00 | 0.00 |
| 0.023 | 0.00 | 0.00 | 0.00 | 0.00 |
| 0.026 | 0.00 | 0.00 | 0.00 | 0.00 |
| 0.030 | 0.00 | 0.00 | 0.00 | 0.00 |
| 0.035 | 0.00 | 0.00 | 0.00 | 0.00 |
| 0.040 | 0.00 | 0.00 | 0.00 | 0.00 |
| 0.046 | 0.00 | 0.00 | 0.00 | 0.00 |
| 0.052 | 0.00 | 0.00 | 0.00 | 0.00 |
| 0.060 | 0.00 | 0.00 | 0.00 | 0.00 |

TABLE 8-continued

Particle sizes of the first granule fraction for experiment V (mixing time of 75 min prior to granulation) determined by laser diffraction and shown as a function of the roller compaction force.

| | Volume in % (v/v) Exp. V | | | |
|---|---|---|---|---|
| Size (μm) | 4 kN/cm | 7 kN/cm | 10 kN/cm | 13 kN/cm |
| 0.069 | 0.00 | 0.00 | 0.00 | 0.00 |
| 0.079 | 0.00 | 0.00 | 0.00 | 0.00 |
| 0.091 | 0.00 | 0.00 | 0.00 | 0.00 |
| 0.105 | 0.00 | 0.00 | 0.00 | 0.00 |
| 0.120 | 0.00 | 0.00 | 0.00 | 0.00 |
| 0.138 | 0.00 | 0.00 | 0.00 | 0.00 |
| 0.158 | 0.00 | 0.00 | 0.00 | 0.00 |
| 0.182 | 0.00 | 0.00 | 0.00 | 0.00 |
| 0.209 | 0.00 | 0.00 | 0.00 | 0.00 |
| 0.240 | 0.00 | 0.00 | 0.00 | 0.00 |
| 0.275 | 0.00 | 0.00 | 0.00 | 0.00 |
| 0.316 | 0.00 | 0.00 | 0.00 | 0.00 |
| 0.363 | 0.00 | 0.00 | 0.00 | 0.00 |
| 0.417 | 0.00 | 0.00 | 0.00 | 0.00 |
| 0.479 | 0.00 | 0.00 | 0.00 | 0.00 |
| 0.550 | 0.02 | 0.00 | 0.00 | 0.00 |
| 0.631 | 0.09 | 0.05 | 0.00 | 0.05 |
| 0.724 | 0.15 | 0.12 | 0.02 | 0.13 |
| 0.832 | 0.24 | 0.23 | 0.07 | 0.23 |
| 0.955 | 0.34 | 0.33 | 0.11 | 0.33 |
| 1.096 | 0.47 | 0.46 | 0.16 | 0.45 |
| 1.259 | 0.63 | 0.60 | 0.19 | 0.59 |
| 1.445 | 0.81 | 0.76 | 0.25 | 0.73 |
| 1.660 | 1.03 | 0.93 | 0.41 | 0.90 |
| 1.905 | 1.27 | 1.11 | 0.54 | 1.07 |
| 2.188 | 1.53 | 1.30 | 0.66 | 1.24 |
| 2.512 | 1.80 | 1.47 | 0.76 | 1.40 |
| 2.884 | 2.07 | 1.63 | 0.84 | 1.55 |
| 3.311 | 2.31 | 1.76 | 0.89 | 1.68 |
| 3.802 | 2.51 | 1.86 | 0.92 | 1.77 |
| 4.365 | 2.65 | 1.91 | 0.93 | 1.83 |
| 5.012 | 2.71 | 1.91 | 0.92 | 1.84 |
| 5.754 | 2.67 | 1.86 | 0.89 | 1.80 |
| 6.607 | 2.56 | 1.77 | 0.84 | 1.72 |
| 7.586 | 2.35 | 1.63 | 0.79 | 1.60 |
| 8.710 | 2.09 | 1.46 | 0.74 | 1.45 |
| 10.000 | 1.78 | 1.27 | 0.68 | 1.28 |
| 11.482 | 1.47 | 1.08 | 0.63 | 1.11 |
| 13.183 | 1.16 | 0.90 | 0.59 | 0.95 |
| 15.136 | 0.89 | 0.76 | 0.57 | 0.82 |
| 17.378 | 0.68 | 0.66 | 0.56 | 0.73 |
| 19.953 | 0.55 | 0.61 | 0.57 | 0.68 |
| 22.909 | 0.48 | 0.61 | 0.61 | 0.69 |
| 26.303 | 0.47 | 0.65 | 0.68 | 0.73 |
| 30.200 | 0.50 | 0.73 | 0.76 | 0.80 |
| 34.674 | 0.55 | 0.82 | 0.85 | 0.89 |
| 39.811 | 0.62 | 0.93 | 0.96 | 0.98 |
| 45.709 | 0.69 | 1.05 | 1.08 | 1.06 |
| 52.481 | 0.76 | 1.18 | 1.20 | 1.15 |
| 60.256 | 0.84 | 1.33 | 1.35 | 1.24 |
| 69.183 | 0.94 | 1.49 | 1.52 | 1.34 |
| 79.433 | 1.06 | 1.68 | 1.71 | 1.48 |
| 91.201 | 1.23 | 1.91 | 1.95 | 1.66 |
| 104.713 | 1.44 | 2.18 | 2.24 | 1.87 |
| 120.226 | 1.69 | 2.48 | 2.57 | 2.12 |
| 138.038 | 1.99 | 2.84 | 2.97 | 2.39 |
| 158.489 | 2.31 | 3.24 | 3.42 | 2.67 |
| 181.970 | 2.63 | 3.69 | 3.92 | 2.96 |
| 208.930 | 2.92 | 4.16 | 4.44 | 3.23 |
| 239.883 | 3.15 | 4.63 | 4.95 | 3.50 |
| 275.423 | 3.30 | 5.03 | 5.37 | 3.74 |
| 316.228 | 3.36 | 5.31 | 5.67 | 3.93 |
| 363.078 | 3.32 | 5.37 | 5.75 | 4.05 |
| 416.869 | 3.20 | 5.16 | 5.60 | 4.06 |
| 478.630 | 3.04 | 4.63 | 5.21 | 3.96 |
| 549.541 | 2.90 | 3.80 | 4.62 | 3.75 |
| 630.957 | 2.81 | 2.76 | 3.92 | 3.45 |
| 724.436 | 2.80 | 1.63 | 3.21 | 3.11 |
| 831.764 | 2.83 | 0.80 | 2.57 | 2.75 |
| 954.993 | 2.84 | 0.60 | 2.04 | 2.39 |
| 1096.478 | 2.74 | 0.40 | 1.61 | 2.02 |
| 1258.925 | 2.44 | 0.25 | 1.24 | 1.73 |
| 1445.440 | 1.94 | 0.14 | 0.88 | 1.39 |
| 1659.570 | 1.14 | 0.07 | 0.49 | 0.82 |
| 1905.461 | 0.28 | 0.01 | 0.12 | 0.20 |
| 2187.762 | 0.00 | 0.00 | 0.00 | 0.00 |
| 2511.886 | 0.00 | 0.00 | 0.00 | 0.00 |
| 2884.032 | 0.00 | 0.00 | 0.00 | 0.00 |
| 3311.311 | 0.00 | 0.00 | 0.00 | 0.00 |
| 3801.894 | 0.00 | 0.00 | 0.00 | 0.00 |
| 4365.158 | 0.00 | 0.00 | 0.00 | 0.00 |
| 5011.872 | 0.00 | 0.00 | 0.00 | 0.00 |
| 5754.399 | 0.00 | 0.00 | 0.00 | 0.00 |
| 6606.934 | 0.00 | 0.00 | 0.00 | 0.00 |
| 7585.776 | 0.00 | 0.00 | 0.00 | 0.00 |
| 8709.636 | 0.00 | 0.00 | 0.00 | 0.00 |
| 10000.000 | 0.00 | 0.00 | 0.00 | 0.00 |

TABLE 9

Particle sizes of the first granule fraction for experiment VI (mixing time of 20 min prior to granulation) determined by laser diffraction and shown as a function of the roller compaction force.

| | Volume in % (v/v) Exp. VI | | | |
|---|---|---|---|---|
| Size (μm) | 4 kN/cm | 7 kN/cm | 10 kN/cm | 13 kN/cm |
| 0.011 | 0.00 | 0.00 | 0.00 | 0.00 |
| 0.013 | 0.00 | 0.00 | 0.00 | 0.00 |
| 0.015 | 0.00 | 0.00 | 0.00 | 0.00 |
| 0.017 | 0.00 | 0.00 | 0.00 | 0.00 |
| 0.020 | 0.00 | 0.00 | 0.00 | 0.00 |
| 0.023 | 0.00 | 0.00 | 0.00 | 0.00 |
| 0.026 | 0.00 | 0.00 | 0.00 | 0.00 |
| 0.030 | 0.00 | 0.00 | 0.00 | 0.00 |
| 0.035 | 0.00 | 0.00 | 0.00 | 0.00 |
| 0.040 | 0.00 | 0.00 | 0.00 | 0.00 |
| 0.046 | 0.00 | 0.00 | 0.00 | 0.00 |
| 0.052 | 0.00 | 0.00 | 0.00 | 0.00 |
| 0.060 | 0.00 | 0.00 | 0.00 | 0.00 |
| 0.069 | 0.00 | 0.00 | 0.00 | 0.00 |
| 0.079 | 0.00 | 0.00 | 0.00 | 0.00 |
| 0.091 | 0.00 | 0.00 | 0.00 | 0.00 |
| 0.105 | 0.00 | 0.00 | 0.00 | 0.00 |
| 0.120 | 0.00 | 0.00 | 0.00 | 0.00 |
| 0.138 | 0.00 | 0.00 | 0.00 | 0.00 |
| 0.158 | 0.00 | 0.00 | 0.00 | 0.00 |
| 0.182 | 0.00 | 0.00 | 0.00 | 0.00 |
| 0.209 | 0.00 | 0.00 | 0.00 | 0.00 |
| 0.240 | 0.00 | 0.00 | 0.00 | 0.00 |
| 0.275 | 0.00 | 0.00 | 0.00 | 0.00 |
| 0.316 | 0.00 | 0.00 | 0.00 | 0.00 |
| 0.363 | 0.00 | 0.00 | 0.00 | 0.00 |
| 0.417 | 0.00 | 0.00 | 0.00 | 0.00 |
| 0.479 | 0.00 | 0.00 | 0.00 | 0.00 |
| 0.550 | 0.00 | 0.00 | 0.00 | 0.00 |
| 0.631 | 0.07 | 0.05 | 0.00 | 0.00 |
| 0.724 | 0.17 | 0.12 | 0.02 | 0.02 |
| 0.832 | 0.30 | 0.22 | 0.07 | 0.06 |
| 0.955 | 0.43 | 0.30 | 0.10 | 0.10 |
| 1.096 | 0.59 | 0.39 | 0.15 | 0.14 |
| 1.259 | 0.77 | 0.49 | 0.18 | 0.17 |
| 1.445 | 0.97 | 0.59 | 0.23 | 0.21 |
| 1.660 | 1.19 | 0.69 | 0.37 | 0.33 |
| 1.905 | 1.43 | 0.80 | 0.50 | 0.44 |
| 2.188 | 1.67 | 0.90 | 0.61 | 0.53 |
| 2.512 | 1.92 | 1.00 | 0.70 | 0.61 |

TABLE 9-continued

Particle sizes of the first granule fraction for experiment VI (mixing time of 20 min prior to granulation) determined by laser diffraction and shown as a function of the roller compaction force.

| | Volume in % (v/v) Exp. VI | | | |
|---|---|---|---|---|
| Size (μm) | 4 kN/cm | 7 kN/cm | 10 kN/cm | 13 kN/cm |
| 2.884 | 2.14 | 1.08 | 0.77 | 0.68 |
| 3.311 | 2.33 | 1.15 | 0.82 | 0.73 |
| 3.802 | 2.48 | 1.20 | 0.85 | 0.76 |
| 4.365 | 2.55 | 1.23 | 0.85 | 0.77 |
| 5.012 | 2.55 | 1.23 | 0.84 | 0.77 |
| 5.754 | 2.47 | 1.20 | 0.82 | 0.76 |
| 6.607 | 2.32 | 1.15 | 0.79 | 0.74 |
| 7.586 | 2.10 | 1.07 | 0.75 | 0.71 |
| 8.710 | 1.84 | 0.98 | 0.70 | 0.68 |
| 10.000 | 1.55 | 0.87 | 0.67 | 0.65 |
| 11.482 | 1.27 | 0.77 | 0.63 | 0.62 |
| 13.183 | 1.01 | 0.67 | 0.61 | 0.61 |
| 15.136 | 0.80 | 0.60 | 0.60 | 0.60 |
| 17.378 | 0.66 | 0.56 | 0.61 | 0.62 |
| 19.953 | 0.58 | 0.55 | 0.64 | 0.65 |
| 22.909 | 0.56 | 0.58 | 0.69 | 0.70 |
| 26.303 | 0.59 | 0.63 | 0.76 | 0.78 |
| 30.200 | 0.65 | 0.71 | 0.85 | 0.87 |
| 34.674 | 0.73 | 0.81 | 0.95 | 0.98 |
| 39.811 | 0.82 | 0.92 | 1.07 | 1.10 |
| 45.709 | 0.92 | 1.03 | 1.21 | 1.24 |
| 52.481 | 1.03 | 1.16 | 1.36 | 1.39 |
| 60.256 | 1.15 | 1.30 | 1.54 | 1.55 |
| 69.183 | 1.30 | 1.46 | 1.73 | 1.74 |
| 79.433 | 1.49 | 1.65 | 1.96 | 1.95 |
| 91.201 | 1.71 | 1.88 | 2.21 | 2.18 |
| 104.713 | 1.98 | 2.17 | 2.51 | 2.46 |
| 120.226 | 2.30 | 2.51 | 2.86 | 2.77 |
| 138.038 | 2.65 | 2.93 | 3.26 | 3.13 |
| 158.489 | 3.03 | 3.42 | 3.70 | 3.54 |
| 181.970 | 3.42 | 3.96 | 4.22 | 4.01 |
| 208.930 | 3.80 | 4.52 | 4.76 | 4.50 |
| 239.883 | 4.14 | 5.06 | 5.32 | 5.01 |
| 275.423 | 4.38 | 5.51 | 5.82 | 5.47 |
| 316.228 | 4.49 | 5.80 | 6.20 | 5.81 |
| 363.078 | 4.43 | 5.85 | 6.35 | 5.95 |
| 416.869 | 4.16 | 5.63 | 6.21 | 5.83 |
| 478.630 | 3.70 | 5.14 | 5.74 | 5.43 |
| 549.541 | 3.09 | 4.42 | 4.96 | 4.78 |
| 630.957 | 2.40 | 3.57 | 3.96 | 3.96 |
| 724.436 | 1.70 | 2.70 | 2.86 | 3.10 |
| 831.764 | 1.08 | 1.91 | 1.81 | 2.31 |
| 954.993 | 0.66 | 1.28 | 0.92 | 1.66 |
| 1096.478 | 0.54 | 0.80 | 0.26 | 1.16 |
| 1258.925 | 0.42 | 0.47 | 0.08 | 0.79 |
| 1445.440 | 0.31 | 0.24 | 0.01 | 0.52 |
| 1659.570 | 0.16 | 0.11 | 0.00 | 0.27 |
| 1905.461 | 0.04 | 0.03 | 0.00 | 0.06 |
| 2187.762 | 0.00 | 0.00 | 0.00 | 0.00 |
| 2511.886 | 0.00 | 0.00 | 0.00 | 0.00 |
| 2884.032 | 0.00 | 0.00 | 0.00 | 0.00 |
| 3311.311 | 0.00 | 0.00 | 0.00 | 0.00 |
| 3801.894 | 0.00 | 0.00 | 0.00 | 0.00 |
| 4365.158 | 0.00 | 0.00 | 0.00 | 0.00 |
| 5011.872 | 0.00 | 0.00 | 0.00 | 0.00 |
| 5754.399 | 0.00 | 0.00 | 0.00 | 0.00 |
| 6606.934 | 0.00 | 0.00 | 0.00 | 0.00 |
| 7585.776 | 0.00 | 0.00 | 0.00 | 0.00 |
| 8709.636 | 0.00 | 0.00 | 0.00 | 0.00 |
| 10000.000 | 0.00 | 0.00 | 0.00 | 0.00 |

TABLE 10

Particle sizes of the first granule fraction for experiment VII (mixing time of 50 min prior to granulation) determined by laser diffraction and shown as a function of the roller compaction force.

| | Volume in % (v/v) Exp. VII | | |
|---|---|---|---|
| Size (μm) | 4 kN/cm | 7 kN/cm | 10 kN/cm |
| 0.011 | 0.00 | 0.00 | 0.00 |
| 0.013 | 0.00 | 0.00 | 0.00 |
| 0.015 | 0.00 | 0.00 | 0.00 |
| 0.017 | 0.00 | 0.00 | 0.00 |
| 0.020 | 0.00 | 0.00 | 0.00 |
| 0.023 | 0.00 | 0.00 | 0.00 |
| 0.026 | 0.00 | 0.00 | 0.00 |
| 0.030 | 0.00 | 0.00 | 0.00 |
| 0.035 | 0.00 | 0.00 | 0.00 |
| 0.040 | 0.00 | 0.00 | 0.00 |
| 0.046 | 0.00 | 0.00 | 0.00 |
| 0.052 | 0.00 | 0.00 | 0.00 |
| 0.060 | 0.00 | 0.00 | 0.00 |
| 0.069 | 0.00 | 0.00 | 0.00 |
| 0.079 | 0.00 | 0.00 | 0.00 |
| 0.091 | 0.00 | 0.00 | 0.00 |
| 0.105 | 0.00 | 0.00 | 0.00 |
| 0.120 | 0.00 | 0.00 | 0.00 |
| 0.138 | 0.00 | 0.00 | 0.00 |
| 0.158 | 0.00 | 0.00 | 0.00 |
| 0.182 | 0.00 | 0.00 | 0.00 |
| 0.209 | 0.00 | 0.00 | 0.00 |
| 0.240 | 0.00 | 0.00 | 0.00 |
| 0.275 | 0.00 | 0.00 | 0.00 |
| 0.316 | 0.00 | 0.00 | 0.00 |
| 0.363 | 0.00 | 0.00 | 0.00 |
| 0.417 | 0.00 | 0.00 | 0.00 |
| 0.479 | 0.00 | 0.00 | 0.00 |
| 0.550 | 0.00 | 0.00 | 0.00 |
| 0.631 | 0.07 | 0.03 | 0.00 |
| 0.724 | 0.17 | 0.10 | 0.02 |
| 0.832 | 0.30 | 0.22 | 0.07 |
| 0.955 | 0.43 | 0.32 | 0.10 |
| 1.096 | 0.59 | 0.43 | 0.15 |
| 1.259 | 0.76 | 0.54 | 0.18 |
| 1.445 | 0.95 | 0.66 | 0.23 |
| 1.660 | 1.16 | 0.78 | 0.38 |
| 1.905 | 1.39 | 0.89 | 0.51 |
| 2.188 | 1.63 | 1.00 | 0.63 |
| 2.512 | 1.86 | 1.10 | 0.72 |
| 2.884 | 2.07 | 1.19 | 0.79 |
| 3.311 | 2.25 | 1.26 | 0.84 |
| 3.802 | 2.39 | 1.30 | 0.87 |
| 4.365 | 2.46 | 1.32 | 0.88 |
| 5.012 | 2.46 | 1.32 | 0.87 |
| 5.754 | 2.38 | 1.28 | 0.84 |
| 6.607 | 2.24 | 1.22 | 0.81 |
| 7.586 | 2.02 | 1.14 | 0.77 |
| 8.710 | 1.77 | 1.05 | 0.74 |
| 10.000 | 1.49 | 0.95 | 0.70 |
| 11.482 | 1.22 | 0.85 | 0.67 |
| 13.183 | 0.96 | 0.76 | 0.65 |
| 15.136 | 0.76 | 0.70 | 0.64 |
| 17.378 | 0.62 | 0.66 | 0.65 |
| 19.953 | 0.54 | 0.66 | 0.69 |
| 22.909 | 0.52 | 0.69 | 0.74 |
| 26.303 | 0.55 | 0.75 | 0.82 |
| 30.200 | 0.62 | 0.84 | 0.92 |
| 34.674 | 0.70 | 0.95 | 1.03 |
| 39.811 | 0.79 | 1.07 | 1.16 |
| 45.709 | 0.88 | 1.21 | 1.30 |
| 52.481 | 0.99 | 1.36 | 1.46 |
| 60.256 | 1.10 | 1.53 | 1.64 |
| 69.183 | 1.24 | 1.72 | 1.84 |
| 79.433 | 1.41 | 1.94 | 2.08 |
| 91.201 | 1.63 | 2.20 | 2.36 |
| 104.713 | 1.90 | 2.51 | 2.69 |
| 120.226 | 2.21 | 2.86 | 3.07 |
| 138.038 | 2.57 | 3.26 | 3.50 |
| 158.489 | 2.94 | 3.71 | 3.97 |
| 181.970 | 3.33 | 4.21 | 4.46 |

TABLE 10-continued

Particle sizes of the first granule fraction for experiment VII (mixing time of 50 min prior to granulation) determined by laser diffraction and shown as a function of the roller compaction force.

| Size (μm) | Volume in % (v/v) Exp. VII | | |
|---|---|---|---|
| | 4 kN/cm | 7 kN/cm | 10 kN/cm |
| 208.930 | 3.69 | 4.71 | 4.95 |
| 239.883 | 3.98 | 5.20 | 5.39 |
| 275.423 | 4.17 | 5.60 | 5.73 |
| 316.228 | 4.22 | 5.84 | 5.90 |
| 363.078 | 4.10 | 5.85 | 5.85 |
| 416.869 | 3.82 | 5.56 | 5.55 |
| 478.630 | 3.40 | 4.95 | 5.00 |
| 549.541 | 2.91 | 4.06 | 4.25 |
| 630.957 | 2.41 | 2.98 | 3.39 |
| 724.436 | 1.98 | 1.86 | 2.51 |
| 831.764 | 1.64 | 0.75 | 1.72 |
| 954.993 | 1.39 | 0.10 | 1.07 |
| 1096.478 | 1.23 | 0.00 | 0.59 |
| 1258.925 | 1.12 | 0.00 | 0.32 |
| 1445.440 | 0.91 | 0.00 | 0.20 |
| 1659.570 | 0.54 | 0.00 | 0.10 |
| 1905.461 | 0.13 | 0.00 | 0.03 |
| 2187.762 | 0.00 | 0.00 | 0.00 |
| 2511.886 | 0.00 | 0.00 | 0.00 |
| 2884.032 | 0.00 | 0.00 | 0.00 |
| 3311.311 | 0.00 | 0.00 | 0.00 |
| 3801.894 | 0.00 | 0.00 | 0.00 |
| 4365.158 | 0.00 | 0.00 | 0.00 |
| 5011.872 | 0.00 | 0.00 | 0.00 |
| 5754.399 | 0.00 | 0.00 | 0.00 |
| 6606.934 | 0.00 | 0.00 | 0.00 |
| 7585.776 | 0.00 | 0.00 | 0.00 |
| 8709.636 | 0.00 | 0.00 | 0.00 |
| 10000.000 | 0.00 | 0.00 | 0.00 |

TABLE 11

Particle sizes of the first granule fraction for experiment VIII (mixing time of 75 min prior to granulation) determined by laser diffraction and shown as a function of the roller compaction force.

| Size (μm) | Volume in % (v/v) Exp. VIII | | | |
|---|---|---|---|---|
| | 4 kN/cm | 7 kN/cm | 10 kN/cm | 13 kN/cm |
| 0.011 | 0.00 | 0.00 | 0.00 | 0.00 |
| 0.013 | 0.00 | 0.00 | 0.00 | 0.00 |
| 0.015 | 0.00 | 0.00 | 0.00 | 0.00 |
| 0.017 | 0.00 | 0.00 | 0.00 | 0.00 |
| 0.020 | 0.00 | 0.00 | 0.00 | 0.00 |
| 0.023 | 0.00 | 0.00 | 0.00 | 0.00 |
| 0.026 | 0.00 | 0.00 | 0.00 | 0.00 |
| 0.030 | 0.00 | 0.00 | 0.00 | 0.00 |
| 0.035 | 0.00 | 0.00 | 0.00 | 0.00 |
| 0.040 | 0.00 | 0.00 | 0.00 | 0.00 |
| 0.046 | 0.00 | 0.00 | 0.00 | 0.00 |
| 0.052 | 0.00 | 0.00 | 0.00 | 0.00 |
| 0.060 | 0.00 | 0.00 | 0.00 | 0.00 |
| 0.069 | 0.00 | 0.00 | 0.00 | 0.00 |
| 0.079 | 0.00 | 0.00 | 0.00 | 0.00 |
| 0.091 | 0.00 | 0.00 | 0.00 | 0.00 |
| 0.105 | 0.00 | 0.00 | 0.00 | 0.00 |
| 0.120 | 0.00 | 0.00 | 0.00 | 0.00 |
| 0.138 | 0.00 | 0.00 | 0.00 | 0.00 |
| 0.158 | 0.00 | 0.00 | 0.00 | 0.00 |
| 0.182 | 0.00 | 0.00 | 0.00 | 0.00 |
| 0.209 | 0.00 | 0.00 | 0.00 | 0.00 |
| 0.240 | 0.00 | 0.00 | 0.00 | 0.00 |
| 0.275 | 0.00 | 0.00 | 0.00 | 0.00 |
| 0.316 | 0.00 | 0.00 | 0.00 | 0.00 |
| 0.363 | 0.00 | 0.00 | 0.00 | 0.00 |
| 0.417 | 0.00 | 0.00 | 0.00 | 0.00 |
| 0.479 | 0.00 | 0.00 | 0.00 | 0.00 |
| 0.550 | 0.00 | 0.00 | 0.00 | 0.00 |
| 0.631 | 0.07 | 0.06 | 0.02 | 0.01 |
| 0.724 | 0.18 | 0.13 | 0.06 | 0.08 |
| 0.832 | 0.31 | 0.23 | 0.09 | 0.14 |
| 0.955 | 0.44 | 0.32 | 0.13 | 0.23 |
| 1.096 | 0.59 | 0.43 | 0.16 | 0.30 |
| 1.259 | 0.75 | 0.54 | 0.20 | 0.39 |
| 1.445 | 0.93 | 0.65 | 0.25 | 0.47 |
| 1.660 | 1.13 | 0.77 | 0.40 | 0.56 |
| 1.905 | 1.33 | 0.89 | 0.53 | 0.65 |
| 2.188 | 1.54 | 1.01 | 0.65 | 0.73 |
| 2.512 | 1.75 | 1.12 | 0.75 | 0.81 |
| 2.884 | 1.93 | 1.22 | 0.83 | 0.89 |
| 3.311 | 2.09 | 1.30 | 0.89 | 0.95 |
| 3.802 | 2.20 | 1.35 | 0.92 | 0.99 |
| 4.365 | 2.26 | 1.38 | 0.93 | 1.02 |
| 5.012 | 2.25 | 1.38 | 0.92 | 1.04 |
| 5.754 | 2.18 | 1.35 | 0.89 | 1.03 |
| 6.607 | 2.06 | 1.30 | 0.86 | 1.00 |
| 7.586 | 1.88 | 1.22 | 0.81 | 0.96 |
| 8.710 | 1.67 | 1.13 | 0.77 | 0.90 |
| 10.000 | 1.45 | 1.04 | 0.73 | 0.84 |
| 11.482 | 1.25 | 0.96 | 0.71 | 0.78 |
| 13.183 | 1.07 | 0.89 | 0.69 | 0.74 |
| 15.136 | 0.94 | 0.86 | 0.70 | 0.72 |
| 17.378 | 0.88 | 0.87 | 0.73 | 0.74 |
| 19.953 | 0.88 | 0.92 | 0.79 | 0.78 |
| 22.909 | 0.95 | 1.02 | 0.87 | 0.86 |
| 26.303 | 1.08 | 1.15 | 0.97 | 0.97 |
| 30.200 | 1.23 | 1.31 | 1.10 | 1.10 |
| 34.674 | 1.41 | 1.47 | 1.24 | 1.23 |
| 39.811 | 1.57 | 1.63 | 1.38 | 1.36 |
| 45.709 | 1.73 | 1.77 | 1.53 | 1.48 |
| 52.481 | 1.86 | 1.90 | 1.67 | 1.59 |
| 60.256 | 1.96 | 2.00 | 1.81 | 1.69 |
| 69.183 | 2.04 | 2.10 | 1.93 | 1.78 |
| 79.433 | 2.10 | 2.18 | 2.05 | 1.87 |
| 91.201 | 2.16 | 2.28 | 2.18 | 1.96 |
| 104.713 | 2.23 | 2.39 | 2.31 | 2.06 |
| 120.226 | 2.32 | 2.55 | 2.48 | 2.20 |
| 138.038 | 2.45 | 2.75 | 2.70 | 2.39 |
| 158.489 | 2.62 | 3.02 | 3.00 | 2.65 |
| 181.970 | 2.85 | 3.35 | 3.42 | 3.02 |
| 208.930 | 3.11 | 3.74 | 3.94 | 3.50 |
| 239.883 | 3.41 | 4.18 | 4.57 | 4.09 |
| 275.423 | 3.69 | 4.60 | 5.22 | 4.73 |
| 316.228 | 3.91 | 4.95 | 5.82 | 5.34 |
| 363.078 | 4.00 | 5.13 | 6.23 | 5.80 |
| 416.869 | 3.91 | 5.07 | 6.33 | 6.00 |
| 478.630 | 3.60 | 4.72 | 6.02 | 5.85 |
| 549.541 | 3.09 | 4.08 | 5.28 | 5.33 |
| 630.957 | 2.43 | 3.21 | 4.20 | 4.50 |
| 724.436 | 1.68 | 2.24 | 2.87 | 3.49 |
| 831.764 | 0.98 | 1.28 | 1.60 | 2.45 |
| 954.993 | 0.58 | 0.47 | 0.90 | 1.52 |
| 1096.478 | 0.44 | 0.13 | 0.53 | 0.80 |
| 1258.925 | 0.31 | 0.00 | 0.28 | 0.35 |
| 1445.440 | 0.21 | 0.00 | 0.11 | 0.19 |
| 1659.570 | 0.10 | 0.00 | 0.01 | 0.08 |
| 1905.461 | 0.03 | 0.00 | 0.00 | 0.02 |
| 2187.762 | 0.00 | 0.00 | 0.00 | 0.00 |
| 2511.886 | 0.00 | 0.00 | 0.00 | 0.00 |
| 2884.032 | 0.00 | 0.00 | 0.00 | 0.00 |
| 3311.311 | 0.00 | 0.00 | 0.00 | 0.00 |
| 3801.894 | 0.00 | 0.00 | 0.00 | 0.00 |
| 4365.158 | 0.00 | 0.00 | 0.00 | 0.00 |
| 5011.872 | 0.00 | 0.00 | 0.00 | 0.00 |
| 5754.399 | 0.00 | 0.00 | 0.00 | 0.00 |
| 6606.934 | 0.00 | 0.00 | 0.00 | 0.00 |
| 7585.776 | 0.00 | 0.00 | 0.00 | 0.00 |

TABLE 11-continued

Particle sizes of the first granule fraction for experiment VIII (mixing time of 75 min prior to granulation) determined by laser diffraction and shown as a function of the roller compaction force.

| | Volume in % (v/v) Exp. VIII | | | |
|---|---|---|---|---|
| Size (μm) | 4 kN/cm | 7 kN/cm | 10 kN/cm | 13 kN/cm |
| 8709.636 | 0.00 | 0.00 | 0.00 | 0.00 |
| 10000.000 | 0.00 | 0.00 | 0.00 | 0.00 |

TABLE 12

Particle sizes of the first granule fraction for experiment IX (mixing time of 55 min prior to granulation) determined by laser diffraction and shown as a function of the roller compaction force.

| | Volume in % (v/v) Exp. IX | | | |
|---|---|---|---|---|
| Size (μm) | 4 kN/cm | 7 kN/cm | 10 kN/cm | 13 kN/cm |
| 0.011 | 0.00 | 0.00 | 0.00 | 0.00 |
| 0.013 | 0.00 | 0.00 | 0.00 | 0.00 |
| 0.015 | 0.00 | 0.00 | 0.00 | 0.00 |
| 0.017 | 0.00 | 0.00 | 0.00 | 0.00 |
| 0.020 | 0.00 | 0.00 | 0.00 | 0.00 |
| 0.023 | 0.00 | 0.00 | 0.00 | 0.00 |
| 0.026 | 0.00 | 0.00 | 0.00 | 0.00 |
| 0.030 | 0.00 | 0.00 | 0.00 | 0.00 |
| 0.035 | 0.00 | 0.00 | 0.00 | 0.00 |
| 0.040 | 0.00 | 0.00 | 0.00 | 0.00 |
| 0.046 | 0.00 | 0.00 | 0.00 | 0.00 |
| 0.052 | 0.00 | 0.00 | 0.00 | 0.00 |
| 0.060 | 0.00 | 0.00 | 0.00 | 0.00 |
| 0.069 | 0.00 | 0.00 | 0.00 | 0.00 |
| 0.079 | 0.00 | 0.00 | 0.00 | 0.00 |
| 0.091 | 0.00 | 0.00 | 0.00 | 0.00 |
| 0.105 | 0.00 | 0.00 | 0.00 | 0.00 |
| 0.120 | 0.00 | 0.00 | 0.00 | 0.00 |
| 0.138 | 0.00 | 0.00 | 0.00 | 0.00 |
| 0.158 | 0.00 | 0.00 | 0.00 | 0.00 |
| 0.182 | 0.00 | 0.00 | 0.00 | 0.00 |
| 0.209 | 0.00 | 0.00 | 0.00 | 0.00 |
| 0.240 | 0.00 | 0.00 | 0.00 | 0.00 |
| 0.275 | 0.00 | 0.00 | 0.00 | 0.00 |
| 0.316 | 0.00 | 0.00 | 0.00 | 0.00 |
| 0.363 | 0.00 | 0.00 | 0.00 | 0.00 |
| 0.417 | 0.00 | 0.00 | 0.00 | 0.00 |
| 0.479 | 0.00 | 0.00 | 0.00 | 0.00 |
| 0.550 | 0.00 | 0.00 | 0.00 | 0.00 |
| 0.631 | 0.06 | 0.05 | 0.00 | 0.00 |
| 0.724 | 0.15 | 0.12 | 0.05 | 0.02 |
| 0.832 | 0.27 | 0.21 | 0.13 | 0.06 |
| 0.955 | 0.38 | 0.29 | 0.23 | 0.09 |
| 1.096 | 0.53 | 0.37 | 0.31 | 0.13 |
| 1.259 | 0.69 | 0.47 | 0.40 | 0.15 |
| 1.445 | 0.86 | 0.56 | 0.48 | 0.20 |
| 1.660 | 1.06 | 0.65 | 0.56 | 0.33 |
| 1.905 | 1.26 | 0.75 | 0.63 | 0.44 |
| 2.188 | 1.47 | 0.84 | 0.70 | 0.54 |
| 2.512 | 1.67 | 0.93 | 0.76 | 0.63 |
| 2.884 | 1.86 | 1.00 | 0.81 | 0.70 |
| 3.311 | 2.01 | 1.06 | 0.85 | 0.75 |
| 3.802 | 2.12 | 1.10 | 0.89 | 0.78 |
| 4.365 | 2.18 | 1.13 | 0.90 | 0.79 |
| 5.012 | 2.18 | 1.13 | 0.91 | 0.79 |
| 5.754 | 2.11 | 1.11 | 0.90 | 0.78 |
| 6.607 | 1.98 | 1.07 | 0.88 | 0.76 |
| 7.586 | 1.81 | 1.02 | 0.85 | 0.73 |
| 8.710 | 1.60 | 0.95 | 0.81 | 0.69 |
| 10.000 | 1.38 | 0.89 | 0.77 | 0.66 |
| 11.482 | 1.18 | 0.83 | 0.74 | 0.64 |
| 13.183 | 1.01 | 0.78 | 0.71 | 0.63 |
| 15.136 | 0.89 | 0.76 | 0.71 | 0.63 |
| 17.378 | 0.83 | 0.77 | 0.73 | 0.66 |
| 19.953 | 0.84 | 0.82 | 0.78 | 0.70 |
| 22.909 | 0.92 | 0.90 | 0.86 | 0.78 |
| 26.303 | 1.05 | 1.02 | 0.96 | 0.87 |
| 30.200 | 1.21 | 1.16 | 1.09 | 0.98 |
| 34.674 | 1.39 | 1.31 | 1.22 | 1.11 |
| 39.811 | 1.56 | 1.47 | 1.36 | 1.25 |
| 45.709 | 1.72 | 1.63 | 1.50 | 1.39 |
| 52.481 | 1.86 | 1.77 | 1.64 | 1.54 |
| 60.256 | 1.98 | 1.91 | 1.77 | 1.69 |
| 69.183 | 2.07 | 2.04 | 1.88 | 1.83 |
| 79.433 | 2.15 | 2.16 | 2.00 | 1.98 |
| 91.201 | 2.22 | 2.28 | 2.11 | 2.12 |
| 104.713 | 2.32 | 2.43 | 2.24 | 2.27 |
| 120.226 | 2.44 | 2.60 | 2.39 | 2.44 |
| 138.038 | 2.60 | 2.83 | 2.60 | 2.66 |
| 158.489 | 2.80 | 3.13 | 2.90 | 2.94 |
| 181.970 | 3.05 | 3.52 | 3.31 | 3.33 |
| 208.930 | 3.33 | 4.01 | 3.84 | 3.82 |
| 239.883 | 3.62 | 4.58 | 4.48 | 4.44 |
| 275.423 | 3.87 | 5.16 | 5.16 | 5.12 |
| 316.228 | 4.03 | 5.67 | 5.80 | 5.78 |
| 363.078 | 4.05 | 5.98 | 6.24 | 6.29 |
| 416.869 | 3.90 | 5.98 | 6.38 | 6.53 |
| 478.630 | 3.56 | 5.57 | 6.11 | 6.39 |
| 549.541 | 3.06 | 4.75 | 5.41 | 5.83 |
| 630.957 | 2.44 | 3.56 | 4.38 | 4.90 |
| 724.436 | 1.79 | 2.19 | 3.13 | 3.74 |
| 831.764 | 1.18 | 0.73 | 1.87 | 2.52 |
| 954.993 | 0.66 | 0.00 | 0.75 | 1.42 |
| 1096.478 | 0.33 | 0.00 | 0.12 | 0.56 |
| 1258.925 | 0.22 | 0.00 | 0.00 | 0.19 |
| 1445.440 | 0.14 | 0.00 | 0.00 | 0.02 |
| 1659.570 | 0.07 | 0.00 | 0.00 | 0.00 |
| 1905.461 | 0.02 | 0.00 | 0.00 | 0.00 |
| 2187.762 | 0.00 | 0.00 | 0.00 | 0.00 |
| 2511.886 | 0.00 | 0.00 | 0.00 | 0.00 |
| 2884.032 | 0.00 | 0.00 | 0.00 | 0.00 |
| 3311.311 | 0.00 | 0.00 | 0.00 | 0.00 |
| 3801.894 | 0.00 | 0.00 | 0.00 | 0.00 |
| 4365.158 | 0.00 | 0.00 | 0.00 | 0.00 |
| 5011.872 | 0.00 | 0.00 | 0.00 | 0.00 |
| 5754.399 | 0.00 | 0.00 | 0.00 | 0.00 |
| 6606.934 | 0.00 | 0.00 | 0.00 | 0.00 |
| 7585.776 | 0.00 | 0.00 | 0.00 | 0.00 |
| 8709.636 | 0.00 | 0.00 | 0.00 | 0.00 |
| 10000.000 | 0.00 | 0.00 | 0.00 | 0.00 |

TABLE 13

Particle sizes of the first granule fraction for experiment X (mixing time of 70 min prior to granulation) determined by laser diffraction and shown as a function of the roller compaction force.

| | Volume in % (v/v) Exp. X | | |
|---|---|---|---|
| Size (μm) | 4 kN/cm | 7 kN/cm | 10 kN/cm |
| 0.011 | 0.00 | 0.00 | 0.00 |
| 0.013 | 0.00 | 0.00 | 0.00 |
| 0.015 | 0.00 | 0.00 | 0.00 |
| 0.017 | 0.00 | 0.00 | 0.00 |
| 0.020 | 0.00 | 0.00 | 0.00 |
| 0.023 | 0.00 | 0.00 | 0.00 |
| 0.026 | 0.00 | 0.00 | 0.00 |
| 0.030 | 0.00 | 0.00 | 0.00 |
| 0.035 | 0.00 | 0.00 | 0.00 |
| 0.040 | 0.00 | 0.00 | 0.00 |

TABLE 13-continued

Particle sizes of the first granule fraction for experiment X (mixing time of 70 min prior to granulation) determined by laser diffraction and shown as a function of the roller compaction force.

| Size (μm) | Volume in % (v/v) Exp. X | | |
|---|---|---|---|
| | 4 kN/cm | 7 kN/cm | 10 kN/cm |
| 0.046 | 0.00 | 0.00 | 0.00 |
| 0.052 | 0.00 | 0.00 | 0.00 |
| 0.060 | 0.00 | 0.00 | 0.00 |
| 0.069 | 0.00 | 0.00 | 0.00 |
| 0.079 | 0.00 | 0.00 | 0.00 |
| 0.091 | 0.00 | 0.00 | 0.00 |
| 0.105 | 0.00 | 0.00 | 0.00 |
| 0.120 | 0.00 | 0.00 | 0.00 |
| 0.138 | 0.00 | 0.00 | 0.00 |
| 0.158 | 0.00 | 0.00 | 0.00 |
| 0.182 | 0.00 | 0.00 | 0.00 |
| 0.209 | 0.00 | 0.00 | 0.00 |
| 0.240 | 0.00 | 0.00 | 0.00 |
| 0.275 | 0.00 | 0.00 | 0.00 |
| 0.316 | 0.00 | 0.00 | 0.00 |
| 0.363 | 0.00 | 0.00 | 0.00 |
| 0.417 | 0.00 | 0.00 | 0.00 |
| 0.479 | 0.00 | 0.00 | 0.00 |
| 0.550 | 0.00 | 0.00 | 0.00 |
| 0.631 | 0.07 | 0.05 | 0.00 |
| 0.724 | 0.16 | 0.11 | 0.00 |
| 0.832 | 0.28 | 0.19 | 0.00 |
| 0.955 | 0.40 | 0.26 | 0.00 |
| 1.096 | 0.54 | 0.34 | 0.00 |
| 1.259 | 0.70 | 0.43 | 0.00 |
| 1.445 | 0.88 | 0.52 | 0.01 |
| 1.660 | 1.06 | 0.61 | 0.12 |
| 1.905 | 1.26 | 0.69 | 0.30 |
| 2.188 | 1.46 | 0.78 | 0.45 |
| 2.512 | 1.65 | 0.86 | 0.58 |
| 2.884 | 1.82 | 0.94 | 0.67 |
| 3.311 | 1.96 | 1.00 | 0.74 |
| 3.802 | 2.06 | 1.04 | 0.77 |
| 4.365 | 2.10 | 1.07 | 0.77 |
| 5.012 | 2.09 | 1.08 | 0.75 |
| 5.754 | 2.02 | 1.06 | 0.71 |
| 6.607 | 1.89 | 1.03 | 0.66 |
| 7.586 | 1.73 | 0.99 | 0.62 |
| 8.710 | 1.54 | 0.93 | 0.58 |
| 10.000 | 1.35 | 0.87 | 0.55 |
| 11.482 | 1.18 | 0.81 | 0.54 |
| 13.183 | 1.03 | 0.77 | 0.54 |
| 15.136 | 0.93 | 0.74 | 0.56 |
| 17.378 | 0.89 | 0.75 | 0.60 |
| 19.953 | 0.92 | 0.78 | 0.65 |
| 22.909 | 1.00 | 0.85 | 0.71 |
| 26.303 | 1.12 | 0.95 | 0.79 |
| 30.200 | 1.28 | 1.08 | 0.89 |
| 34.674 | 1.46 | 1.22 | 1.00 |
| 39.811 | 1.63 | 1.37 | 1.13 |
| 45.709 | 1.78 | 1.52 | 1.26 |
| 52.481 | 1.91 | 1.67 | 1.39 |
| 60.256 | 2.02 | 1.80 | 1.52 |
| 69.183 | 2.09 | 1.92 | 1.64 |
| 79.433 | 2.15 | 2.03 | 1.76 |
| 91.201 | 2.20 | 2.14 | 1.87 |
| 104.713 | 2.27 | 2.26 | 2.01 |
| 120.226 | 2.36 | 2.43 | 2.18 |
| 138.038 | 2.49 | 2.65 | 2.42 |
| 158.489 | 2.66 | 2.96 | 2.74 |
| 181.970 | 2.87 | 3.36 | 3.20 |
| 208.930 | 3.10 | 3.84 | 3.77 |
| 239.883 | 3.31 | 4.36 | 4.45 |
| 275.423 | 3.47 | 4.86 | 5.18 |
| 316.228 | 3.54 | 5.24 | 5.87 |
| 363.078 | 3.46 | 5.42 | 6.40 |
| 416.869 | 3.25 | 5.34 | 6.66 |
| 478.630 | 2.91 | 4.97 | 6.55 |
| 549.541 | 2.50 | 4.35 | 6.07 |
| 630.957 | 2.10 | 3.58 | 5.27 |
| 724.436 | 1.77 | 2.78 | 4.26 |
| 831.764 | 1.54 | 2.07 | 3.19 |
| 954.993 | 1.39 | 1.50 | 2.18 |
| 1096.478 | 1.39 | 1.08 | 1.32 |
| 1258.925 | 1.26 | 0.78 | 0.68 |
| 1445.440 | 1.01 | 0.54 | 0.33 |
| 1659.570 | 0.60 | 0.29 | 0.13 |
| 1905.461 | 0.14 | 0.07 | 0.03 |
| 2187.762 | 0.00 | 0.00 | 0.00 |
| 2511.886 | 0.00 | 0.00 | 0.00 |
| 2884.032 | 0.00 | 0.00 | 0.00 |
| 3311.311 | 0.00 | 0.00 | 0.00 |
| 3801.894 | 0.00 | 0.00 | 0.00 |
| 4365.158 | 0.00 | 0.00 | 0.00 |
| 5011.872 | 0.00 | 0.00 | 0.00 |
| 5754.399 | 0.00 | 0.00 | 0.00 |
| 6606.934 | 0.00 | 0.00 | 0.00 |
| 7585.776 | 0.00 | 0.00 | 0.00 |
| 8709.636 | 0.00 | 0.00 | 0.00 |
| 10000.000 | 0.00 | 0.00 | 0.00 |

The tablet resistance to crushing was determined as described in the section General Methods of Detection and Characterisation. The results are shown in Tables 14-17 as a function of the compression force used to prepare the tablets and as a function of the roller compaction force used to prepare the first granule fraction.

TABLE 14

Tablet resistance to crushing as a function of the compression force for experiment V and the applied roller compaction force for the first granule fraction (mixing time of 75 minutes prior to granulation, Composition Type D).

| Exp. V - 4 kN/cm | | Exp. V - 7 kN/cm | | Exp. V - 13 kN/cm | |
|---|---|---|---|---|---|
| Compression force (kN) | Tablet resistance to crushing (N) | Compression force (kN) | Tablet resistance to crushing (N) | Compression force (kN) | Tablet resistance to crushing (N) |
| 2.7 | 32 | 2.5 | 27 | 2.3 | 18 |
| 3.6 | 44 | 4.4 | 48 | 3.4 | 28 |
| 5.5 | 72 | 6.1 | 68 | 5.2 | 45 |
| 7.8 | 100 | 8.4 | 89 | 6.9 | 64 |
| 9.3 | 118 | 10.2 | 107 | 8.9 | 84 |
| 10.2 | 128 | 11.7 | 120 | 10.7 | 94 |
| 10.8 | 132 | 13.2 | 135 | 11.7 | 99 |
| 11.8 | 143 | — | — | 13.6 | 108 |
| 12.9 | 149 | — | — | — | — |

TABLE 15

Tablet resistance to crushing as a function of the compression force for experiment VI and the applied roller compaction force for the first granule fraction (mixing time of 20 min prior to granulation, Composition Type D).

| Exp. VI - 4 kN/cm | | Exp. VI - 7 kN/cm | | Exp. VI - 13 kN/cm | |
|---|---|---|---|---|---|
| Compression force (kN) | Tablet resistance to crushing (N) | Compression force (kN) | Tablet resistance to crushing (N) | Compression force (kN) | Tablet resistance to crushing (N) |
| 3.0 | 41 | 2.8 | 27 | 3.0 | 16 |
| 4.2 | 56 | 3.4 | 36 | 4.3 | 25 |

TABLE 15-continued

Tablet resistance to crushing as a function of the compression force for experiment VI and the applied roller compaction force for the first granule fraction (mixing time of 20 min prior to granulation, Composition Type D).

| Exp. VI - 4 kN/cm | | Exp. VI - 7 kN/cm | | Exp. VI - 13 kN/cm | |
|---|---|---|---|---|---|
| Compression force (kN) | Tablet resistance to crushing (N) | Compression force (kN) | Tablet resistance to crushing (N) | Compression force (kN) | Tablet resistance to crushing (N) |
| 5.3 | 72 | 4.7 | 54 | 5.9 | 34 |
| 6.6 | 90 | 5.8 | 63 | 8.2 | 49 |
| 8.2 | 106 | 7.1 | 83 | 9.8 | 57 |
| 10.6 | 134 | 9.1 | 102 | 11.6 | 64 |
| 12.0 | 146 | 10.3 | 113 | 12.8 | 70 |
| 13.3 | 152 | 11.5 | 125 | 13.5 | 72 |
| — | — | 13.4 | 134 | — | — |

TABLE 16

Tablet resistance to crushing as a function of the compression force for experiment VIII and the applied roller compaction force for the first granule fraction (mixing time of 75 min prior to granulation, Composition Type E).

| Exp. VIII - 4 kN/cm | | Exp. VIII - 7 kN/cm | | Exp. VIII - 13 kN/cm | |
|---|---|---|---|---|---|
| Compression force (kN) | Tablet resistance to crushing (N) | Compression force (kN) | Tablet resistance to crushing (N) | Compression force (kN) | Tablet resistance to crushing (N) |
| 2.9 | 43 | 2.4 | 26 | 2.7 | 21 |
| 3.8 | 54 | 3.4 | 37 | 3.9 | 32 |
| 4.6 | 70 | 4.4 | 51 | 5.2 | 47 |
| 5.5 | 83 | 5.8 | 67 | 7.5 | 67 |
| 7.0 | 105 | 7.9 | 94 | 10.2 | 86 |
| 8.2 | 123 | 10.4 | 117 | 12.2 | 96 |
| 10.2 | 145 | 12.2 | 124 | 13.4 | 103 |
| 11.8 | 158 | 12.9 | 132 | — | — |
| 13.4 | 165 | 14.0 | 138 | — | — |

TABLE 17

Tablet resistance to crushing as a function of the compression force for experiment IX and the applied roller compaction force for the first granule fraction (mixing time of 55 min prior to granulation, Composition Type E).

| Exp. IX - 4 kN/cm | | Exp. IX - 7 kN/cm | | Exp. IX - 13 kN/cm | |
|---|---|---|---|---|---|
| Compression force (kN) | Tablet resistance to crushing (N) | Compression force (kN) | Tablet resistance to crushing (N) | Compression force (kN) | Tablet resistance to crushing (N) |
| 2.9 | 41 | 3.0 | 31 | 3.0 | 18 |
| 4.0 | 59 | 4.0 | 41 | 4.0 | 27 |
| 5.2 | 80 | 4.9 | 51 | 5.6 | 41 |
| 6.6 | 99 | 6.9 | 79 | 7.6 | 55 |
| 8.5 | 126 | 9.4 | 94 | 10.4 | 74 |
| 10.5 | 146 | 11.2 | 119 | 11.9 | 81 |
| 12.2 | 163 | 13.1 | 135 | 14.1 | 91 |
| 14.0 | 172 | — | — | — | — |

The tablet friability was determined as described in the section General Methods of Detection and Characterisation. The results are shown in Tables 18-21 as a function of the compression force used to prepare the tablets and as a function of the roller compaction force used to prepare the first granule fraction.

TABLE 18

Tablet friability as a function of the compression force for experiment V and the applied roller compaction force for the first granule fraction (mixing time of 75 min prior to granulation prior to granulation, Composition Type D).

| Exp. V - 4 kN/cm | | Exp. V - 7 kN/cm | | Exp. V - 13 kN/cm | |
|---|---|---|---|---|---|
| Compression force (kN) | Tablet friability (% (w/w)) | Compression force (kN) | Tablet friability (% (w/w)) | Compression force (kN) | Tablet friability (% (w/w)) |
| 2.7 | 0.82 | 2.5 | 1.73 | 2.3 | 100.0 |
| 3.6 | 0.39 | 3.4 | 0.56 | 3.4 | 1.67 |
| 5.5 | 0.14 | 4.4 | 0.32 | 5.2 | 0.30 |
| 7.8 | 0.18 | 6.1 | 0.16 | 6.9 | 0.23 |
| — | — | — | — | 8.9 | 0.14 |
| — | — | — | — | 11.7 | 0.15 |

TABLE 19

Tablet friability as a function of the compression force for experiment VI and the applied roller compaction force for the first granule fraction (mixing time of 20 min prior to granulation, Composition Type D).

| Exp. VI - 4 kN/cm | | Exp. VI - 13 kN/cm | |
|---|---|---|---|
| Compression force (kN) | Tablet friability (% (w/w)) | Compression force (kN) | Tablet friability (% (w/w)) |
| 3.0 | 0.46 | 3.0 | 100.0 |
| 4.2 | 0.26 | 4.3 | 8.91 |
| 5.3 | 0.16 | 5.9 | 0.62 |
| 6.6 | 0.12 | 8.2 | 0.36 |
| — | — | 9.8 | 0.24 |
| — | — | 11.6 | 0.21 |

TABLE 20

Tablet friability as a function of the compression force for experiment VIII and the applied roller compaction force for the first granule fraction (mixing time of 75 minutes prior to granulation, Composition Type E).

| Exp. VIII - 4 kN/cm | | Exp. VIII - 7 kN/cm | | Exp. VIII - 13 kN/cm | |
|---|---|---|---|---|---|
| Compression force (kN) | Tablet friability (% (w/w)) | Compression force (kN) | Tablet friability (% (w/w)) | Compression force (kN) | Tablet friability (% (w/w)) |
| 2.9 | 0.23 | 2.4 | 1.25 | 2.7 | 3.10 |
| 3.8 | 0.17 | 3.4 | 0.45 | 3.9 | 0.54 |
| 4.6 | 0.11 | 4.4 | 0.25 | 5.2 | 0.11 |
| 5.5 | — | 5.8 | 0.17 | 7.5 | 0.05 |
| 7.0 | — | 7.9 | — | 10.2 | — |

TABLE 21

Tablet friability as a function of the compression force for experiment IX and the applied roller compaction force for the first granule fraction (mixing time of 55 minutes prior to granulation, Composition Type E).

| Exp. IX - 4 kN/cm | | Exp. IX - 7 kN/cm | | Exp. IX - 13 kN/cm | |
|---|---|---|---|---|---|
| Compression force (kN) | Tablet friability (% (w/w)) | Compression force (kN) | Tablet friability (% (w/w)) | Compression force (kN) | Tablet friability (% (w/w)) |
| 2.9 | 0.15 | 3.0 | 0.70 | 3.0 | 12.00 |
| 4.0 | 0.06 | 4.0 | 0.29 | 4.0 | 1.41 |
| 5.2 | — | 4.9 | — | 5.6 | 0.29 |

TABLE 21-continued

Tablet friability as a function of the compression force for experiment IX and the applied roller compaction force for the first granule fraction (mixing time of 55 minutes prior to granulation, Composition Type E).

| Exp. IX - 4 kN/cm | | Exp. IX - 7 kN/cm | | Exp. IX - 13 kN/cm | |
|---|---|---|---|---|---|
| Compression force (kN) | Tablet friability (% (w/w)) | Compression force (kN) | Tablet friability (% (w/w)) | Compression force (kN) | Tablet friability (% (w/w)) |
| 6.6 | — | 6.9 | — | 7.6 | 0.20 |
| 8.5 | — | 9.4 | — | 10.4 | 0.14 |

The tablet disintegration time was determined as described in the section General Methods of Detection and Characterisation. The results are shown in Tables 22-23 as a function of the compression force used to prepare the tablets and as a function of the roller compaction force used to prepare the first granule fraction.

TABLE 22

Tablet disintegration time as a function of the compression force for experiment VIII and the applied roller compaction force for the first granule fraction (mixing time of 75 min prior to granulation, Composition Type E).

| Exp. VIII - 4 kN/cm | | Exp. VIII - 7 kN/cm | | Exp. VIII - 13 kN/cm | |
|---|---|---|---|---|---|
| Compression force (kN) | Tablet disintegration time (min) | Compression force (kN) | Tablet disintegration time (min) | Compression force (kN) | Tablet disintegration time (min) |
| 2.9 | 9.4 | 2.4 | 7.4 | 2.7 | 7.2 |
| 3.8 | 9.9 | 3.4 | 7.6 | 3.9 | 8.5 |
| 4.6 | 10.6 | 4.4 | 8.9 | 5.2 | 9.4 |
| 5.5 | 11.0 | 5.8 | 9.6 | 7.5 | 10.3 |
| 7.0 | 8.7 | 7.9 | 10.3 | 10.2 | 10.4 |
| 8.2 | 9.1 | 10.4 | 11.2 | 12.2 | 11.7 |
| 10.2 | 9.3 | 12.2 | 11.8 | 13.4 | 10.9 |
| 11.8 | 9.6 | 12.9 | 11.2 | — | — |
| 13.4 | 9.6 | 14.0 | 11.2 | — | — |

TABLE 23

Tablet disintegration time as a function of the compression force for experiment IX and the applied roller compaction force for the first granule fraction (mixing time of 55 min prior to granulation, Composition Type E).

| Exp. IX - 4 kN/cm | | Exp. IX - 7 kN/cm | | Exp. IX - 13 kN/cm | |
|---|---|---|---|---|---|
| Compression force (kN) | Tablet disintegration time (min) | Compression force (kN) | Tablet disintegration time (min) | Compression force (kN) | Tablet disintegration time (min) |
| 2.9 | 6.9 | 3.0 | 8.9 | 3.0 | 10.0 |
| 4.0 | 8.7 | 4.0 | 10.9 | 4.0 | 9.4 |
| 5.2 | 8.6 | 6.9 | 9.3 | 5.6 | 10.0 |
| 6.6 | 10.0 | 9.4 | 12.6 | 7.6 | 10.7 |
| 8.5 | 9.9 | 11.2 | 13.2 | 10.4 | 11.1 |
| 10.5 | 9.4 | 13.1 | 9.0 | 11.9 | 11.6 |
| 12.2 | 9.2 | — | — | 14.1 | 11.6 |
| 14.0 | 8.5 | — | — | — | — |

The results show that the pharmaceutical technical properties of the tablets prepared from Composition Type D were either unaltered or improved when a longer mixing time prior to granulation was used to mix the magnesium stearate and SNAC, i.e. the crushing strength of the tablets was increased or un-altered and the friability of the tablets was unaltered or reduced. In addition, the time used for mixing of the blend of magnesium stearate and SNAC prior to granulation did not influence the size or the extent of granulation.

The results show that the pharmaceutical technical properties of the tablets prepared from Composition Type E were either unaltered or improved when a longer mixing time prior to granulation was used to mix the magnesium stearate, SNAC and microcrystalline cellulose, i.e. the crushing strength of the tablets was increased or unaltered, the friability of the tablets was unaltered or reduced, and the disintegration time of the tablets was unaltered. In addition, the time used for mixing of the blend of magnesium stearate, SNAC, and microcrystalline cellulose prior to granulation did not influence the size or the extent of granulation.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A process of producing by dry granulation a granule comprising a salt of N-(8-(2-hydroxybenzoyl)amino) caprylic acid and a lubricant, wherein said process comprises the steps:
   a) mixing said salt of N-(8-(2-hydroxybenzoyl)amino) caprylic acid and said lubricant for more than 5 minutes; and
   b) optionally roller compacting the mixture of step a, wherein the granule produced by said process does not contain a pharmaceutically active agent.

2. A process according to claim 1, wherein the duration of said mixing in step a is at least 20 minutes.

3. A process according to claim 1, wherein the amount of said lubricant is at least 0.25% (w/w) of said composition.

4. The process according to claim 3, wherein the amount of said lubricant is at least 2.0% (w/w) of said composition.

5. The process according to claim 4, wherein the amount of said lubricant is less than 10.0% (w/w) of said composition.

6. The process according to claim 5, wherein the lubricant is magnesium stearate.

* * * * *

SEQUENCE LISTING

<160> NUMBER OF SEQ ID NOS: 2

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 40
<212> TYPE: PRT
<213> ORGANISM: Heloderma suspectum

<400> SEQUENCE: 2

His Gly Glu Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
        35                  40